(12) United States Patent
Zhou et al.

(10) Patent No.: US 10,626,077 B2
(45) Date of Patent: *Apr. 21, 2020

(54) SALVIANOLIC ACID COMPOUND T, PREPARATION METHOD THEREFOR, AND USE THEREOF

(71) Applicant: TASLY PHARMACEUTICAL GROUP CO., LTD., Tianjin (CN)

(72) Inventors: Shuiping Zhou, Tianjin (CN); Wei Li, Tianjin (CN); Yuanpeng Jin, Tianjin (CN); Xinxin Li, Tianjin (CN); Xiaohui Ma, Tianjin (CN); Wei Zhou, Tianjin (CN); Min Han, Tianjin (CN); Shuming Li, Tianjin (CN)

(73) Assignee: Tasly Pharmaceutical Group Co., LTD., Tianjin (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/914,166

(22) PCT Filed: Aug. 26, 2014

(86) PCT No.: PCT/CN2014/085154
§ 371 (c)(1),
(2) Date: Feb. 24, 2016

(87) PCT Pub. No.: WO2015/027891
PCT Pub. Date: Mar. 5, 2015

(65) Prior Publication Data
US 2016/0200661 A1    Jul. 14, 2016

(30) Foreign Application Priority Data
Aug. 29, 2013  (CN) .......................... 2013 1 0384234

(51) Int. Cl.
C07C 69/732 (2006.01)
C07C 67/56 (2006.01)
A61K 36/537 (2006.01)

(52) U.S. Cl.
CPC .......... *C07C 69/732* (2013.01); *A61K 36/537* (2013.01); *C07C 67/56* (2013.01); *A61K 2236/00* (2013.01); *C07B 2200/09* (2013.01)

(58) Field of Classification Search
None
See application file for complete search history.

(56) References Cited

U.S. PATENT DOCUMENTS 7,438,935 B2   10/2008  Wei et al.
8,343,514 B2   1/2013   Lopez-Goerne
(Continued)

FOREIGN PATENT DOCUMENTS

CN   1421241 A   6/2003
CN   1596920 A   3/2005
(Continued)

OTHER PUBLICATIONS

Liu et al., Pharmaceutical Research (2014), 31(7), 1788-1800.*
(Continued)

*Primary Examiner* — Karl J Puttlitz
(74) *Attorney, Agent, or Firm* — Dilworth & Barrese, LLP

(57) ABSTRACT

The present invention relates to the medical field, specifically a salvianolic acid T as described in structural formula (I), a chiral isomer thereof, a preparation method therefor, pharmaceutical compositions, antioxidants, and free radical scavengers thereof, and a use of the compound.

(Continued)

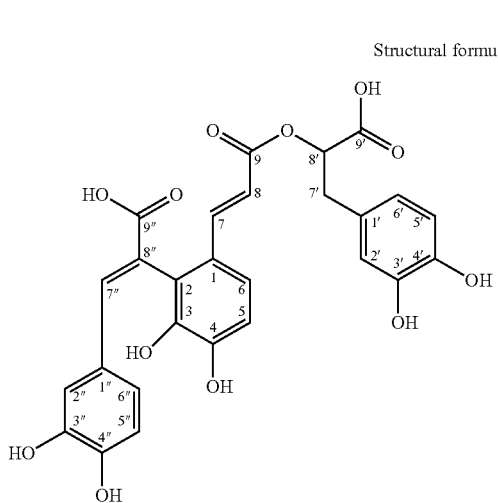

Structural formula (I)

13 Claims, 20 Drawing Sheets

(56) References Cited

U.S. PATENT DOCUMENTS

| | | | |
|---|---|---|---|
| 9,579,293 | B2 | 2/2017 | Venkatesh |
| 2005/0037094 | A1 | 2/2005 | Yan et al. |
| 2007/0071834 | A1 | 3/2007 | Cheng et al. |
| 2007/0218140 | A1 | 9/2007 | Tanabe et al. |
| 2008/0317864 | A1 | 12/2008 | Vila Pena et al. |
| 2010/0076552 | A1 | 3/2010 | Matsuhisa |
| 2011/0135748 | A1 | 6/2011 | Yang et al. |
| 2012/0041062 | A1 | 2/2012 | Zhou et al. |
| 2013/0095164 | A1 | 4/2013 | Lopez-Goerne |
| 2013/0196005 | A1 | 8/2013 | Yan et al. |
| 2016/0143976 | A1 | 5/2016 | Yan et al. |
| 2016/0151293 | A1 | 6/2016 | Yan et al. |
| 2016/0175336 | A1 | 6/2016 | Yan et al. |
| 2016/0184249 | A1 | 6/2016 | Yan et al. |
| 2017/0157156 | A9 | 6/2017 | Yan et al. |

FOREIGN PATENT DOCUMENTS

| | | |
|---|---|---|
| CN | 1600318 A | 3/2005 |
| CN | 1626121 A | 6/2005 |
| CN | 1669573 A | 9/2005 |
| CN | 1714819 A | 1/2006 |
| CN | 1745768 A | 3/2006 |
| CN | 1745769 A | 3/2006 |
| CN | 1759855 A | 4/2006 |
| CN | 1772041 A | 5/2006 |
| CN | 1879697 A | 12/2006 |
| CN | 1927858 A | 3/2007 |
| CN | 1927858 A | 3/2007 |
| CN | 1939406 A | 4/2007 |
| CN | 101020028 A | 8/2007 |
| CN | 101279220 A | 10/2008 |
| CN | 101439076 A | 5/2009 |
| CN | 100512830 C | 7/2009 |
| CN | 101518495 A | 9/2009 |
| CN | 101584743 A | 11/2009 |
| CN | 101612195 A | 12/2009 |
| CN | 102119963 A | 7/2011 |
| CN | 102526186 A | 7/2012 |
| CN | 102526446 A | 7/2012 |
| CN | 102908355 A | 2/2013 |
| CN | 102988476 A | 3/2013 |
| CN | 102119964 B | 11/2016 |
| EP | 1741439 * | 1/2007 |
| EP | 1741439 A1 | 1/2007 |
| EP | 2415749 A1 | 8/2012 |
| EP | 3020407 A1 | 5/2016 |
| EP | 3020408 A1 | 5/2016 |
| EP | 3040077 A1 | 7/2016 |
| JP | 2005306778 A | 11/2005 |
| JP | 2007505936 A | 3/2007 |
| JP | 2008540419 A | 11/2008 |
| JP | 2009511549 A | 3/2009 |
| JP | 2009539819 A | 11/2009 |
| JP | 2012229173 A | 11/2012 |
| TW | 201117839 A | 6/2011 |
| WO | 2008126720 A1 | 10/2008 |
| WO | 2010111935 * | 10/2010 |
| WO | 2010111935 A1 | 10/2010 |
| WO | 2012016549 A1 | 2/2012 |

OTHER PUBLICATIONS

Li et al., Fitoterapia (2014), 98, 248-253.*
Database Caplus Chemical Abstracts Service, Columbus, Ohio, US; Database Accession No. 2014:264648, Abstract of Liu et al., Pharmaceutical Research (2014).*
Database Caplus Chemical Abstracts Service, Columbus, Ohio, US; Database Accession No. 2014:1494351, Abstract of Li et al., Fitoterapia (2014), 98, 248-253.*
Li et al., Fitoterapia 98 (2014) 248-253.*
Kasim, R. et al., "Research on the Water-Soluble Component of the Roots of Salvia Deserta Schang", Journal of Xwjiang Medical University, vol. 25, No. 3, Sep. 30, 2002 (Sep. 30, 2002), p. 234, and figure 1.
International Search Report and Written Opinion dated Jan. 17, 2017.
Lin et al.. "Quantitative Determination of Multi-Components in Compound Danshen Dripping Pill by HPLC Method"; (2011) 413-415.
Wei et al., "Analysis of chemical and metabolic components in traditional Chinese medicinal combined prescription containing Radix Salvia miltiorrhiza and Radix Panax notoginseng by LC-ESL-MS methods"; (2017), Biomedical Chromatography 21: 797-809.
Machine Translation of p. 11, third and forth column of: Qian, Yunxu et al,: The Preparation of Rabdosia serra microdrop pills, Shandong Pharmaceuticaluniverstiy (2003) 22(5): 10-11.
Machine Translation of Abstract of: Wu et al., About Solid Dispersion Technology, 132 (Jan. 19, 2013).
Machine Translation of Abstract of: 7(4): (1997) Chinese Journal of Modern Medical Science China Journal.
Machine Translation of Summary of: 7 (May 3, 1996) Journal: Clinical Observation of nitroglycerin tolerance in elderly patients with corronary heart disease.
Machine Translation of Abstract of p. 315, May 25, 1996: Nitroglycerin induced hypotension in 5 cases; Department of Cardiology, Xijing Hospital, Fourth Military Medical University; He Jiping Chen Schiliang.
Machine Translation of P270 of Pharmacology, in edited by Chen Xingian et al.; San Qi Guan Xin Ning.

* cited by examiner

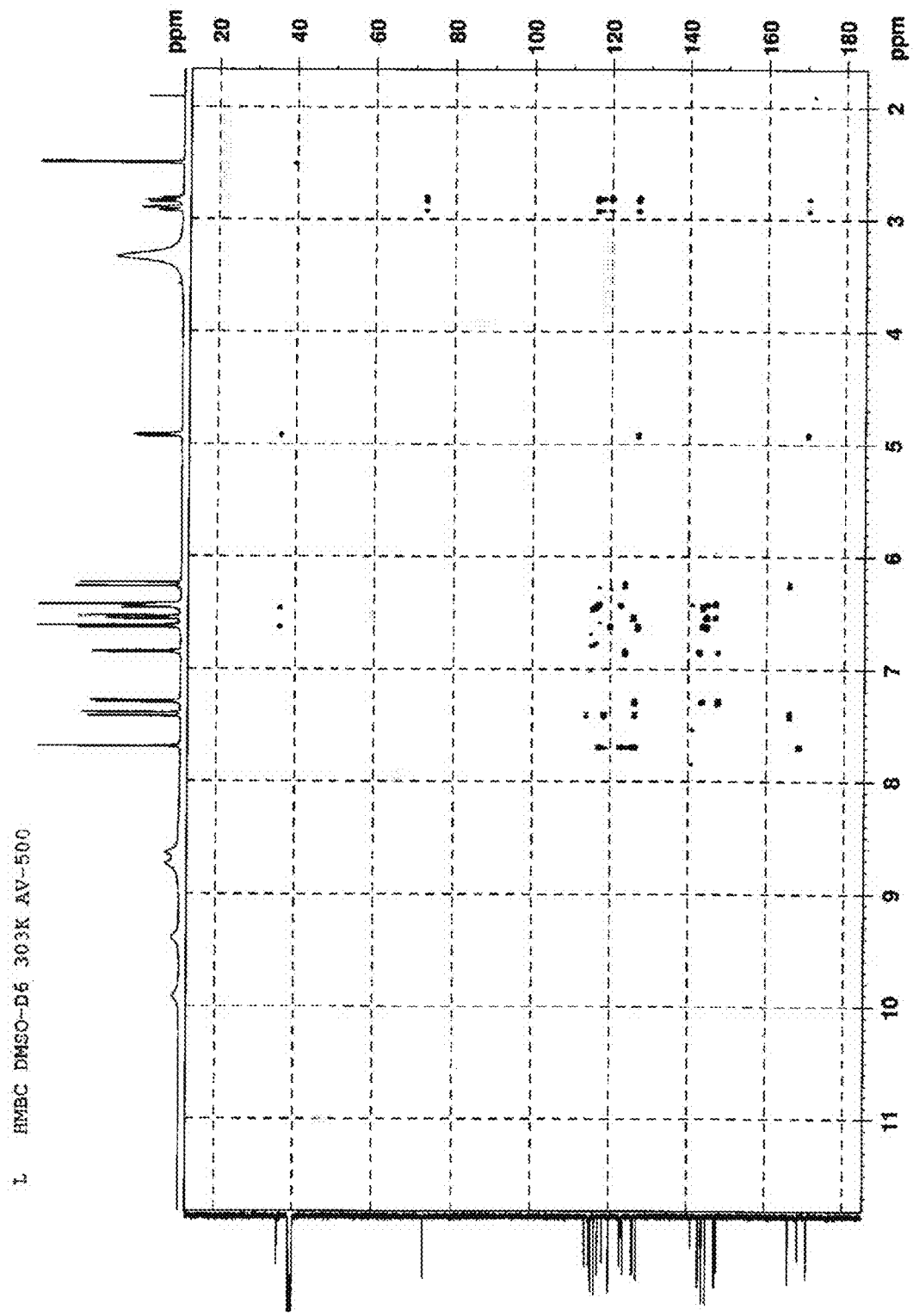

Pseudo operation group

Model group

Aspirin group (S)-salvianolic acid T high-dose group (S)-salvianolic acid T low-dose group

SALVIANOLIC ACID COMPOUND T, PREPARATION METHOD THEREFOR, AND USE THEREOF

FIELD OF THE INVENTION

The present invention relates to the medical field, specifically to a new salvianolic acid compound, a preparation method therefor and a use thereof.

BACKGROUND ART OF THE INVENTION

Radix Salviae Miltiorrhizae is the root of the plants in the genus *Salvia* in Labiatae family, is bitter in taste and a little cold, acting on the channels of heart and liver with the functions of stopping pain by removing stasis, activating blood flow and relieving restlessness by cleaning heart. Modern pharmacological investigations have showed that, Radix Salviae Miltiorrhizae has the effects of dilating coronary artery, improving micro-circulation and protecting heart, and is capable of inhibiting and removing platelet aggregation, increasing body's capability of anoxia tolerance and the activities of anti-hepatitis, anti-tumor and anti-virus etc. In 2001, Institute of Materia Medica, Chinese Academy of Medical Sciences & Peking Union Medical College reported that there were 13 phenolic acid compounds of water-soluble active constituents in Radix Salviae Miltiorrhizae and the same genus plants, including salvianolic acid A, B, C, D, E, F, G, H, I, J, lithospermic acid, rosmarinci acid and isosalvianolic acid C, etc. (Lianniang, Li et al. Bulletin of Medical Research, 2001, Vol. 30(7)), and the pharmacological action of these 13 phenolic acid compounds had also been disclosed. In 2002, Rena. Kasimu et al. reported the chemical structure of salvianolic acid K (Rena. Kasimu et al., Journal of Xinjiang Medical University, 2002, Vol. 25(3)). Foreign researchers have also studied on water-soluble active constituents of Radix Salviae Miltiorrhizae. In 1999, George Washington University had applied and finally been granted a US patent with respect to the effect of 13 salvianolic acid chemical structures on anti-HIV integrase and other viruses, suggesting that Radix Salviae Miltiorrhizae is a medicinal plant resource which has great potential and is worth being developed.

Said salvianolic acid T of the present invention is just a novel compound that has been found in Radix Salviae Miltiorrhizae in the process of massive screening. Up to now, the structure and pharmacological effects relevant to this compound have not yet been reported.

SUMMARY OF THE INVENTION

The objective of the present invention is to provide a salvianolic acid compound T of structural formula (I), its pharmaceutically acceptable salts, solvates and hydrolysable esters.

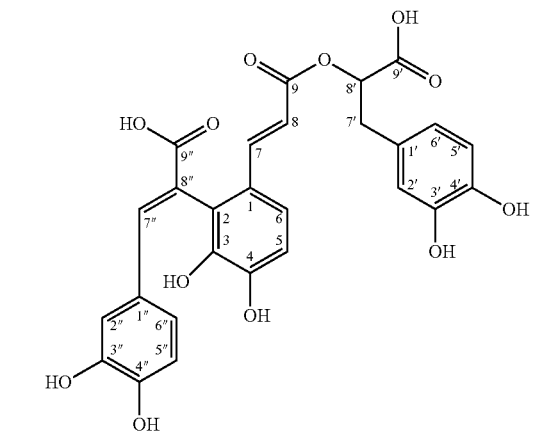

Structural formula (I)

Another objective of the present invention is to provide a preparation method of the salvianolic acid T.

The further objective of the present invention is to provide a pharmaceutical composition, antioxidant, free radical scavenger comprising the salvianolic acid T.

Another objective of the present invention is to provide a use of the salvianolic acid T in the preparation of drugs for treating acute myocardial infarction and acute myocardial ischemia.

Another objective of the present invention is to provide a use of the salvianolic acid T in the preparation of drugs for treating pulmonary fibrosis diseases.

Another objective of the present invention is to provide a use of the salvianolic acid T in the preparation of antioxygens.

Another objective of the present invention is using the salvianolic acid T for treating acute myocardial infarction, acute myocardial ischemia or pulmonary fibrosis diseases.

Another objective of the present invention is using the salvianolic acid T for delaying senility.

Another objective of the present invention is using the salvianolic acid T for antioxidation.

Specifically, the present invention relates to the following (1)-(37) terms of inventions:

[1] A salvianolic acid T represented by the structural formula (I), its pharmaceutically acceptable salts, chiral isomers, solvates and hydrolysable esters.

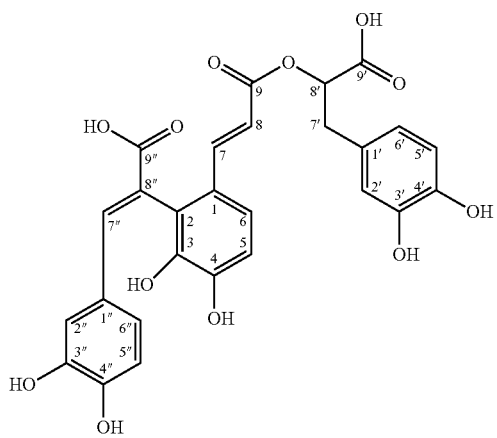

Structural formula (I)

[2] A preparation method of the salvianolic acid T described by [1], wherein, the method includes the following steps:

(1a) extraction: extracting Radix Salviae Miltiorrhizae crude drug or a mixture of Radix Salviae Miltiorrhizae and other crude drugs with water, concentrating the filtrate to obtain a water extract, then adding alcohol to precipitate and obtain a supernatant, concentrating the supernatant to obtain an alcohol extract;

(1b) separation: diluting the alcohol extract of the step (1a) with water, applying on the macroporous absorbent resin, washing the resin with an acidic aqueous solution to remove impurities and then eluting the resin with ethanol to obtain an ethanol eluent, concentrating the ethanol eluent to obtain an extract;

Or, replacing the above steps (1a) and (1b) by the following step (1):

(1) Synthesis: dissolving salvianolic acid B in the water, heating;

(2) purification: adjusting the pH of the reaction liquid obtained in the step (1) to be acidic or purifying the extract obtained in the step (1b) by the preparative high pressure liquid chromatograph, with C18 reversed phase silica gel column as the chromatographic packing, acetonitrile-water-formic acid as the eluent, carrying out isocratic elution or gradient elution, with a detection wavelength of 280 nm; monitoring the elution process by high performance liquid chromatography, collecting the eluent containing salvianolic acid T; concentrating to obtain the salvianolic acid T.

[3] A preparation method of the chiral isomers of salvianolic acid T described as [1], wherein, the method includes the following steps:

(1a) extraction: extracting Radix Salviae Miltiorrhizae crude drug or a mixture of Radix Salviae Miltiorrhizae and other crude drugs with water, concentrating the filtrate to obtain a water extract, then adding alcohol to precipitate and obtain a supernatant, concentrating the supernatant to obtain an alcohol extract;

(1b) separation: diluting the alcohol extract obtained in the step (1a) with water, applying on the macroporous absorbent resin, washing the resin with an acidic aqueous solution to remove impurities and then eluting the resin with ethanol to obtain an ethanol eluent, concentrating the ethanol eluent to obtain an extract;

Or, replacing the above steps (1a) and (1b) by the following step (1):

(1) Synthesis: dissolving salvianolic acid B in the water, heating;

(2) purification: adjusting the pH of the reaction liquid obtained in the step (1) to be acidic or purifying the extract obtained in the step (1b) by the preparative high pressure liquid chromatograph, with C18 reversed phase silica gel column as the chromatographic packing, acetonitrile-water-formic acid as the eluent, carrying out isocratic elution, with a detection wavelength of 280 nm; monitoring the elution process by high performance liquid chromatography, combining the eluent containing salvianolic acid T; concentrating to obtain the salvianolic acid T.

(3) preparation of the chiral isomers: separating the chiral isomers from the salvianolic acid T obtained in step (2) by preparative liquid chromatograph, with reversed phase chiral column as the chromatographic column, acetonitrile-water-formic acid as the eluent, carrying out isocratic elution or gradient elution, with a detection wavelength of 280 nm; monitoring the elution process by high performance liquid chromatography, collecting the eluent containing (S)-salvianolic acid T and (R)-salvianolic acid T separately, freeze-drying to obtain the pure products of (S)-salvianolic acid T and (R)-salvianolic acid T.

[4] The preparation method as described in [2] or [3], wherein, in the step (1a), the said Radix Salviae Miltiorrhizae crude drug or the mixture of Radix Salviae Miltiorrhizae and other crude drugs are decoction pieces, crushed particles or powders, the said other crude drugs are Radix Notoginseng or Radix Astragali or the combination of the two, which are compatible with Radix Salviae Miltiorrhizae.

[5] The preparation method as described in [2] or [3], wherein, in the step (1a), the said water-extraction is as follows: decocting the crude drug with water of 4-8 times the volume of the crude drug for 1.5-4 h; filtrating; concentrating the filtrate to obtain a water extract with a relative density of 1.10-1.30 (80□).

[6] The preparation method as described in [2] or [3], wherein, in the step (1a), the said water-extraction is as follows: decocting the crude drug with water of 6 times the volume of the crude drug for 3 h; filtrating; concentrating the filtrate to obtain a water extract with a relative density of 1.22 (80□).

[7] The preparation method as described in [2] or [3], wherein, in the step (1a), an alkali aqueous solution is used in the said water-extraction step, the said alkali is at least one selected from the group consisting of sodium bicarbonate solution, sodium carbonate aqueous solution, potassium hydrogen carbonate solution, potassium carbonate solution, sodium hydroxide aqueous solution, potassium hydroxide aqueous solution.

[8] The preparation method as described in [7], wherein, the said alkali aqueous solution is a sodium bicarbonate aqueous solution in a concentration of 0.3%-0.45% (w/v).

[9] The preparation method as described in [2] or [3], wherein, in the step (1a), the said alcohol-precipitation is as follows: adding 95% (v/v) ethanol into the water extract to precipitate until the content of the ethanol being 50%-70% (v/v)(25□), and standing still for 8-36 h; obtaining the supernatant, recovering ethanol under reduced pressure condition, concentrating to obtain an alcohol extract with a relative density of 1.25-1.5 (60□).

[10] The preparation method as described in [2] or [3], wherein, in the step (1a), the said alcohol-precipitation is as follows: adding 95% (v/v) ethanol into the water extract to precipitate until the content of the ethanol being 60% (v/v) (25□), and standing still for 24 h; obtaining the supernatant, recovering ethanol under reduced pressure condition, concentrating to obtain an alcohol extract with a relative density of 1.32 (60□).

[11] The preparation method as described in [2] or [3], wherein, in the step (1b), the said macroporous adsorptive resin can be non-polar or weak polar macroporous adsorptive resin.

[12] The preparation method as described in [11], wherein, the non-polar or weak polar macroporous adsorptive resin is AB-8 type, HPD450 type, D101 type, or X5 type macroporous adsorptive resin.

[13] The preparation method as described in [12], wherein, the non-polar or weak polar macroporous adsorptive resin is AB-8 type.

[14] The preparation method as described in [2] or [3], wherein, in the step (1a), the weight ratio of the crude drug to the macroporous absorbent resin is 5:1-1:1.

[15] The preparation method as described in [14], wherein, in the step (1a), the weight ratio of the crude drug to the macroporous absorbent resin is 3:1.

[16] The preparation method as described in [2] or [3], wherein, in the step (1b), the said acidic aqueous solution is at least one selected from the group consisting of hydrochloric acid aqueous solution, sulfuric acid aqueous solution, nitric acid aqueous solution and acetic acid aqueous solution or the combination of them; the pH of the solution is adjusted into 1.0-5.0, washing with the acidic aqueous solution until the eluent being nearly colorless.

[17] The preparation method as described in [16], wherein, the said acidic aqueous solution is hydrochloric acid aqueous solution; the pH of the solution is adjusted into 3.0.

[18] The preparation method as described in [2] or [3], wherein, in the step (1b), 4-10 times of 50%-95% (v/v) ethanol is used to wash the column, then the eluent is concentrated to obtain an extract without alcoholic smell.

[19] The preparation method as described in [18], wherein, 5 times of 95% (v/v) ethanol is used to wash the column.

[20] The preparation method as described in [2] or [3], wherein, in the step (1), the reaction raw material is salvianolic acid B or its salts.

[21] The preparation method as described in [2] or [3], wherein, in the step (1), the mass ratio of the said salvianolic acid B to the said aqueous solution is 1:0.1-1:100000, the reaction temperature is 10-150 □, the reaction time is 10 min to 24 h.

[22] The preparation method as described in [2] or [3], wherein, in the step (1), the mass ratio of the said salvianolic acid B to the said aqueous solution is 1:200, the reaction temperature is 90 □, the reaction time is 1 h.

[23] The preparation method as described in [2] or [3], wherein, in the step (1), the said aqueous solution is acidic aqueous solution, neutral aqueous solution or alkaline aqueous solution.

[24] The preparation method as described in [2] or [3], wherein, in the step (1), the said aqueous solution is alkaline aqueous solution, the said alkaline aqueous solution is at least selected from the following aqueous solutions: sodium bicarbonate solution, sodium carbonate aqueous solution, potassium hydrogen carbonate solution, potassium carbonate solution, sodium hydroxide aqueous solution and potassium hydroxide aqueous solution.

[25] The preparation method as described in [8], wherein, the said alkaline aqueous solution is sodium bicarbonate solution with a concentration of 0.05%-0.45% (w/v).

[26] The preparation method as described in [2] or [3], wherein, in the step (2), any one or combination of the hydrochloric acid aqueous solution, sulfuric acid aqueous solution, aqueous solution of nitric acid and acetic acid aqueous solution is used to adjust the pH of the reaction liquid into 1.0-6.0.

[27] The preparation method as described in [26], wherein, the hydrochloric acid aqueous solution is used to adjust the reaction liquid into 3.0.

[28] The preparation method as described in [2] or [3], wherein, in the step (2), the said high pressure liquid chromatograph is dynamic axial high pressure liquid chromatograph, the chromatographic packing is C18 reversed phase silica gel column, dissolving the reaction liquid the pH of which is adjusted in the step (1) or the extract obtained in the said step (1b) with mobile phase, the said mobile phase is acetonitrile:water:formic acid (volume ratio)=(10:90:1)-(90:10:1); the eluent uses the above ratio of the mobile phase, the elution is isocratic elution or gradient elution; the flow rate is 300 mL/min; the detection wavelength is 280 nm; high performance liquid chromatography is used to monitor the elution process, collecting the components the retention time of which is 21.2-24.0 min, concentrating to dry, obtaining salvianolic acid T sample.

[29] The preparation method as described in [28], wherein, the said mobile phase is acetonitrile:water:formic acid (volume ratio)=(10:90:1)-(50:50:1).

[30] The preparation method as described in [28], wherein, the said mobile phase is acetonitrile:water:formic acid (volume ratio)=15:85:1.

[31] The preparation method as described in [28], wherein, the said elution uses mobile phase with acetonitrile:water:formic acid (volume ratio)=15:85:1 to carry out the isocratic elution.

[32] The preparation method as described in [3], wherein, in the step (3), preparative liquid chromatograph is used to carry out the chiral isomer separation, the chromatographic column is reversed phase column, dissolving the salvianolic acid T sample obtained in the step (2) with mobile phase, the said mobile phase is acetonitrile:water:formic acid (volume ratio)=(90:10:1)-(10:90:1); the eluent uses the above ratio of the mobile phase, the elution is isocratic elution or gradient elution; the flow rate is 25 mL/min; the detection wavelength is 280 nm; high performance liquid chromatography is used to monitor the elution process, collecting the (S)-salvianolic acid T component with a retention time of 19.5-21.1 min, (R)-salvianolic acid T component with a retention time of 23.9-25.3 min separately, freeze-drying after low temperature centration, obtaining (S)-salvianolic acid T pure product and (R)-salvianolic acid T pure product.

[33] The preparation method as described in [32], wherein, the said mobile phase is acetonitrile:water:formic acid (volume ratio)=17:83:1.

[34] The preparation method as described in [32], wherein, the said elution uses the mobile phase of acetonitrile:water:formic acid (volume ratio)=17:83:1 to carry out isocratic elution.

[35] The preparation method as described in [32], wherein, the said low temperature is 10-40□.

[36] The preparation method as described in [32], wherein, the said low temperature is 30□.

[37] A pharmaceutical composition comprising said salvianolic acid T, its pharmaceutically acceptable salts, chiral isomers, solvates and hydrolysable esters described in [1].

[38] An antioxidant comprising the salvianolic acid T, its pharmaceutically acceptable salts, chiral isomers, solvates and hydrolysable esters described in [1].

[39] A free radical scavenger comprising the salvianolic acid T, its pharmaceutically acceptable salts, chiral isomers, solvates and hydrolysable esters described in [1].

[40] A use of the salvianolic acid T, its pharmaceutically acceptable salts, chiral isomers, solvates and hydrolysable esters described in [1] in preparing drugs for treating acute myocardial infarction and acute myocardial ischemia.

[41] A use of the salvianolic acid T, its pharmaceutically acceptable salts, chiral isomers, solvates and hydrolysable esters described in [1] in preparing drugs for treating pulmonary fibrosis disease.

[42] A use of the salvianolic acid T, its pharmaceutically acceptable salts, chiral isomers, solvates and hydrolysable esters described in [1] in preparing antioxidants.

[43] Using the salvianolic acid T, its pharmaceutically acceptable salts, chiral isomers, solvates and hydrolysable esters described in [1] for treating acute myocardial infarction, acute myocardial ischemia or pulmonary fibrosis disease.

[44] Using the salvianolic acid T, its pharmaceutically acceptable salts, chiral isomers, solvates and hydrolysable esters described in [1] for delaying senility.

[45] Using the salvianolic acid T, its pharmaceutically acceptable salts, chiral isomers, solvates and hydrolysable esters described in [1] for antioxidation.

DETAILED DESCRIPTION OF THE INVENTION

Figure 1A:
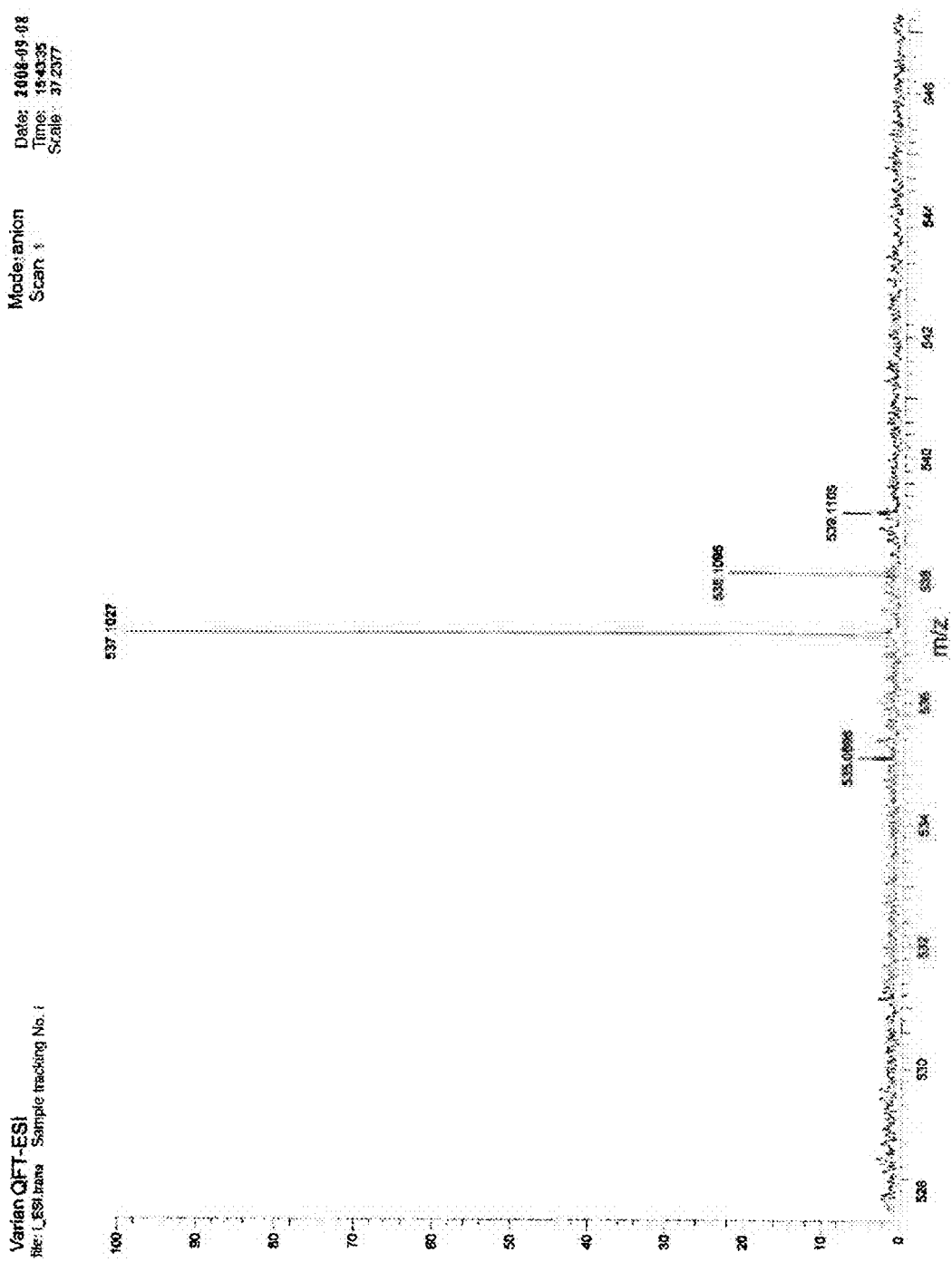
FIG. 1 illustrates the high resolution mass spectrogram of the salvianolic acid T, A: (R)-salvianolic acid T; B: (S)-salvianolic acid T.
Figure 1B:
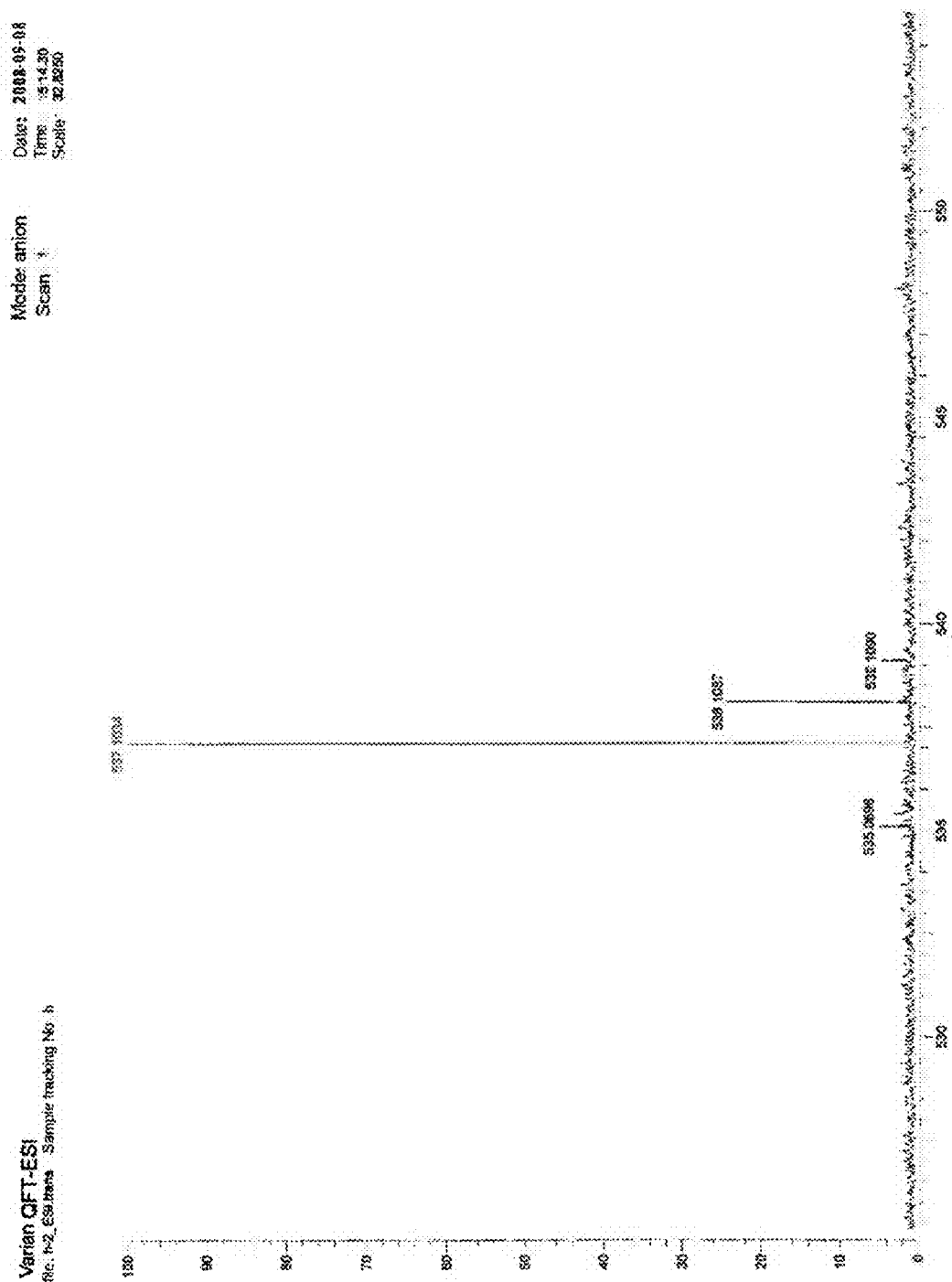
Figure 2A:
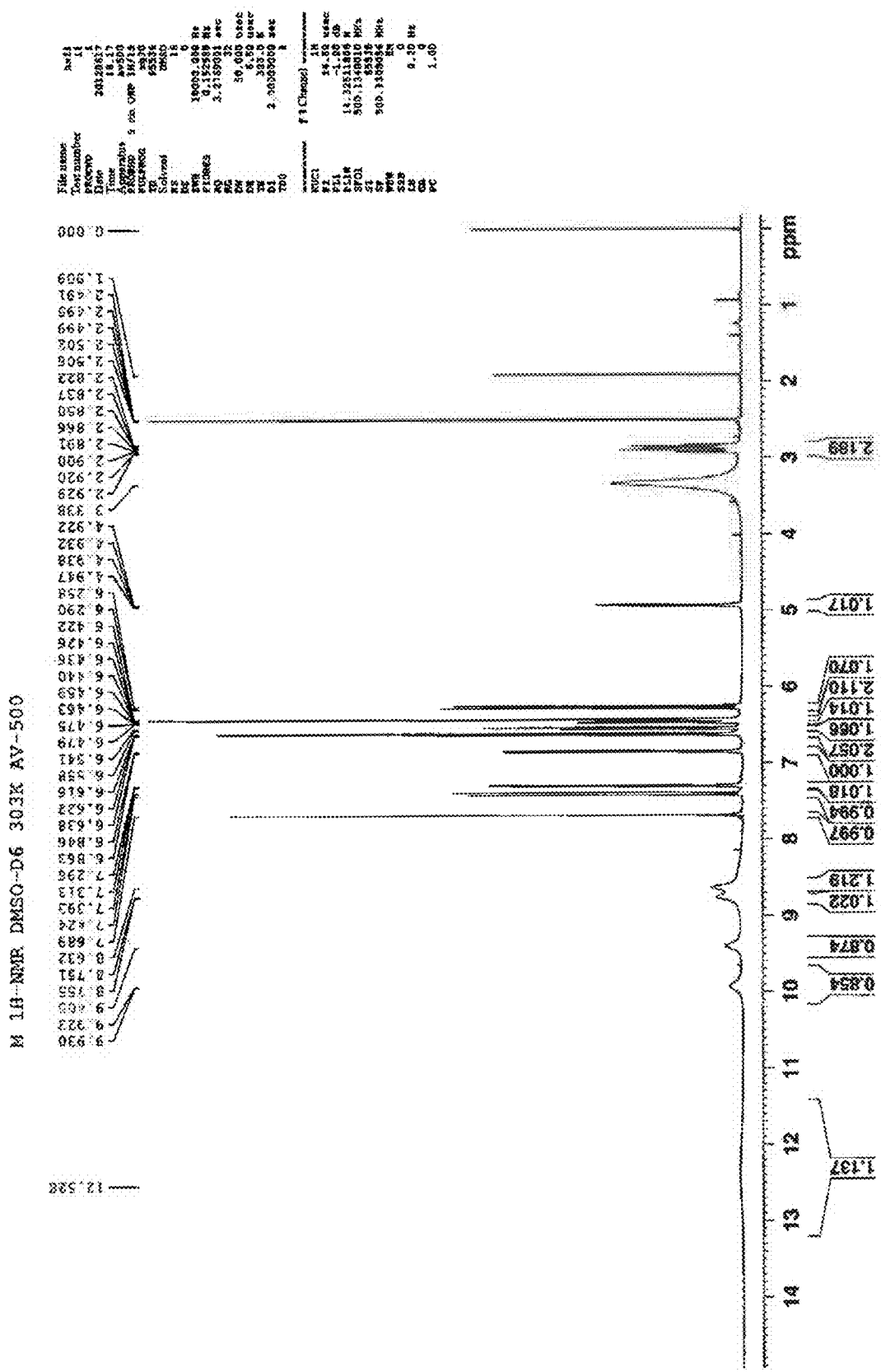
FIG. 2 illustrates the $^1$H-NMR diagram of the salvianolic acid T at 500 MHz, by using DMSO, A: (R)-salvianolic acid T; B: (S)-salvianolic acid T.
Figure 2B:
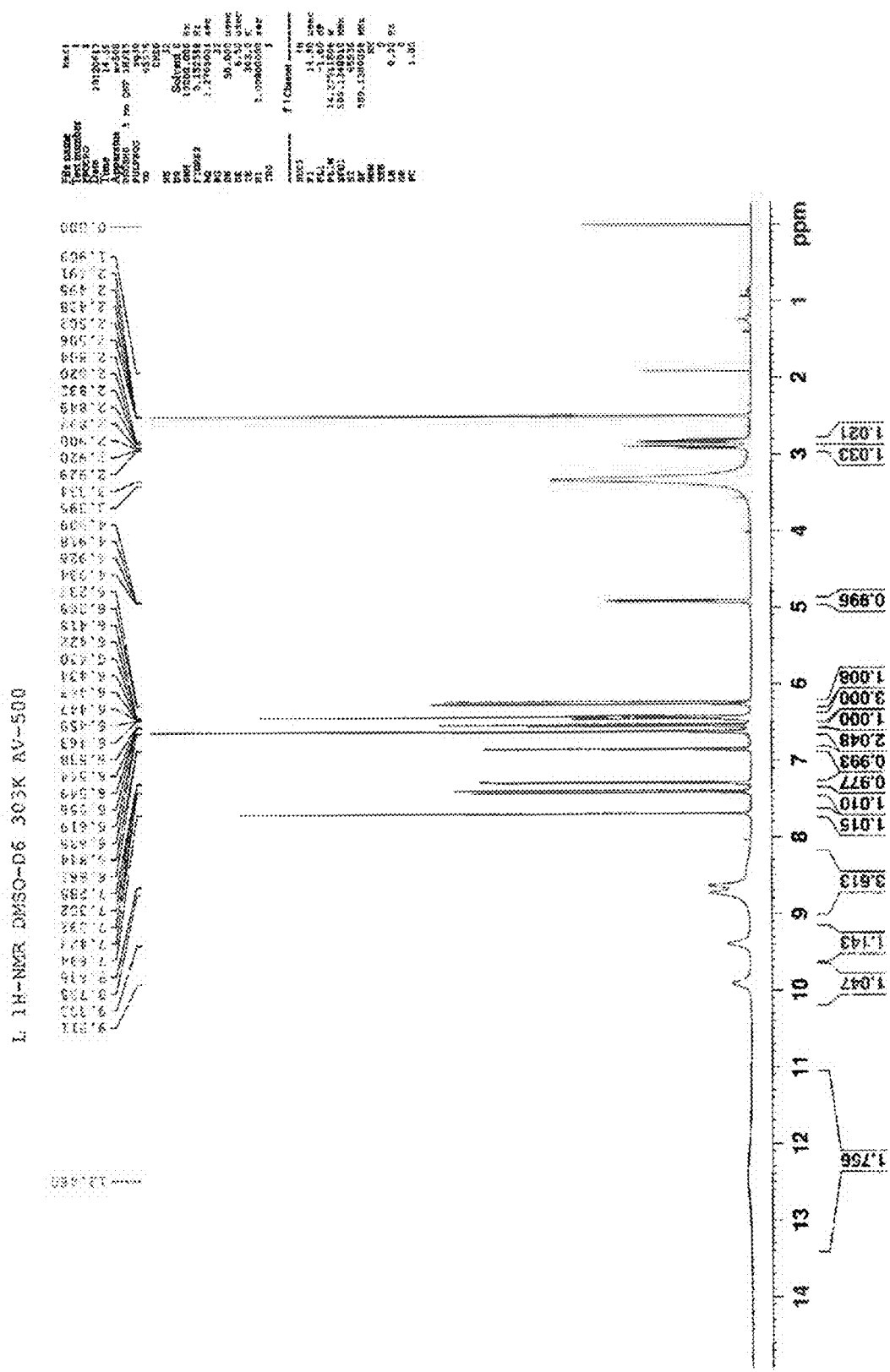
Figure 3A:
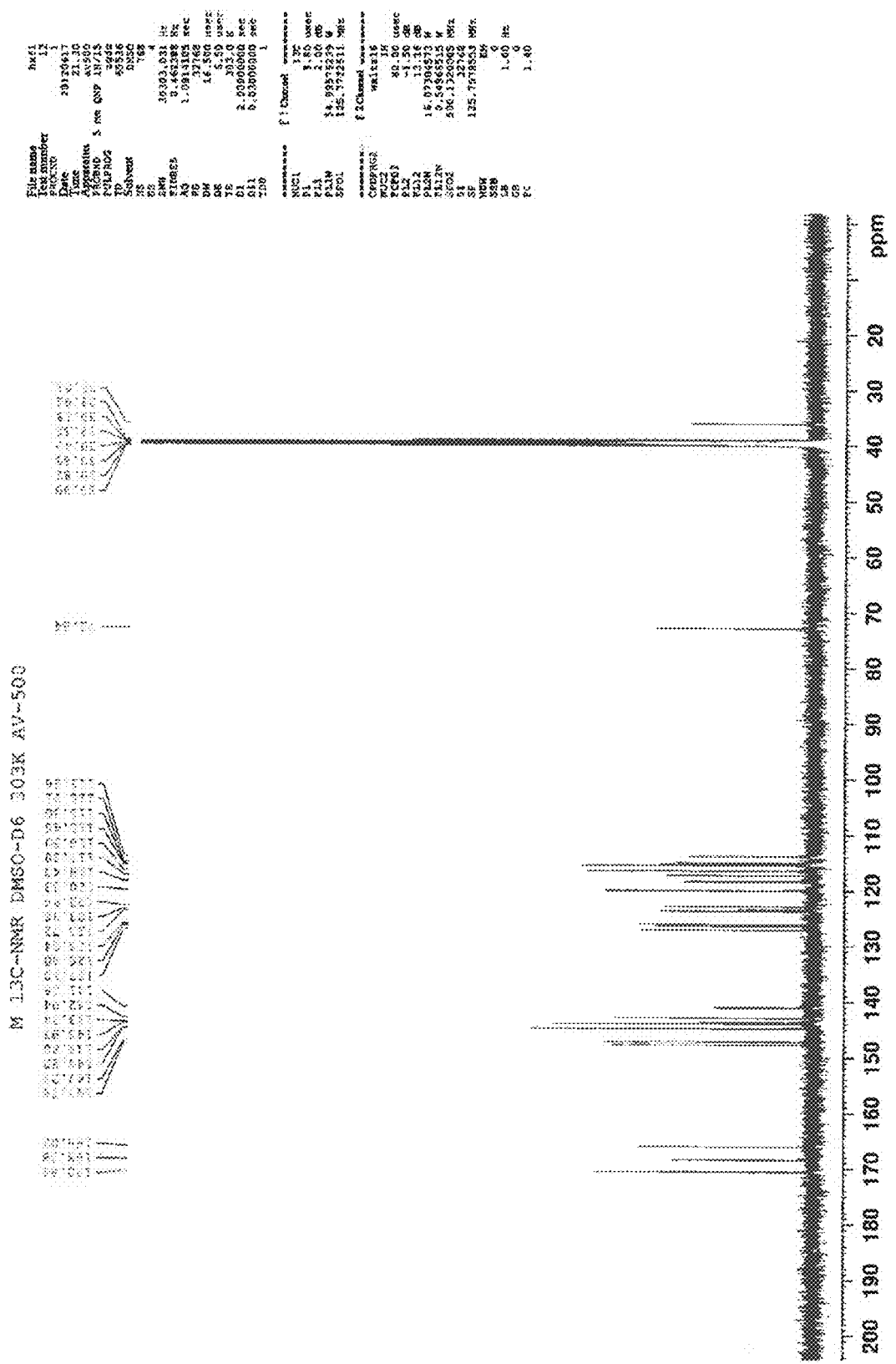
FIG. 3 illustrates the $^{13}$C-NMR diagram of the salvianolic acid T at 125 MHz, by using DMSO, A: (R)-salvianolic acid T; B: (S)-salvianolic acid T.
Figure 3B:
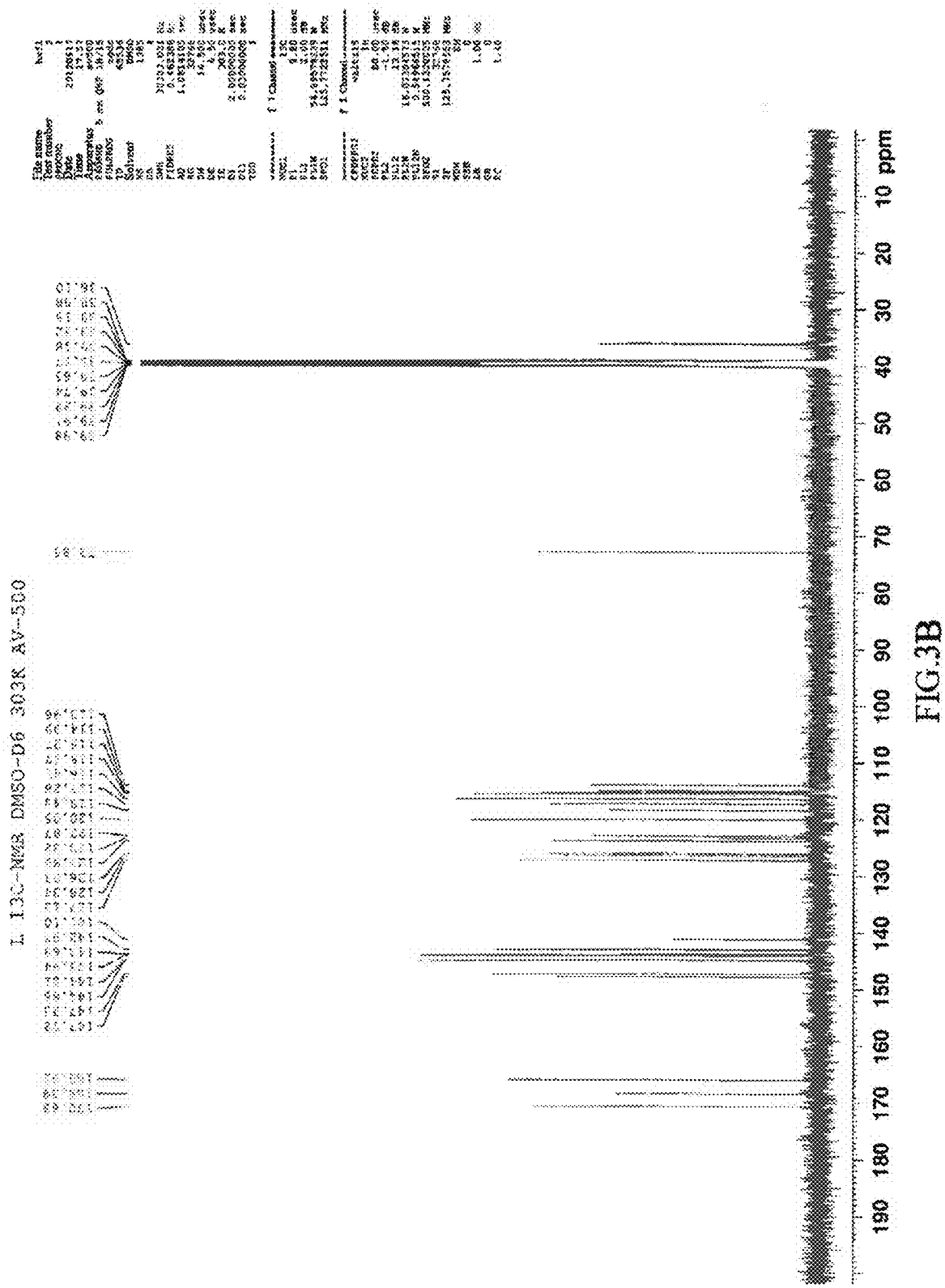
Figure 4A:
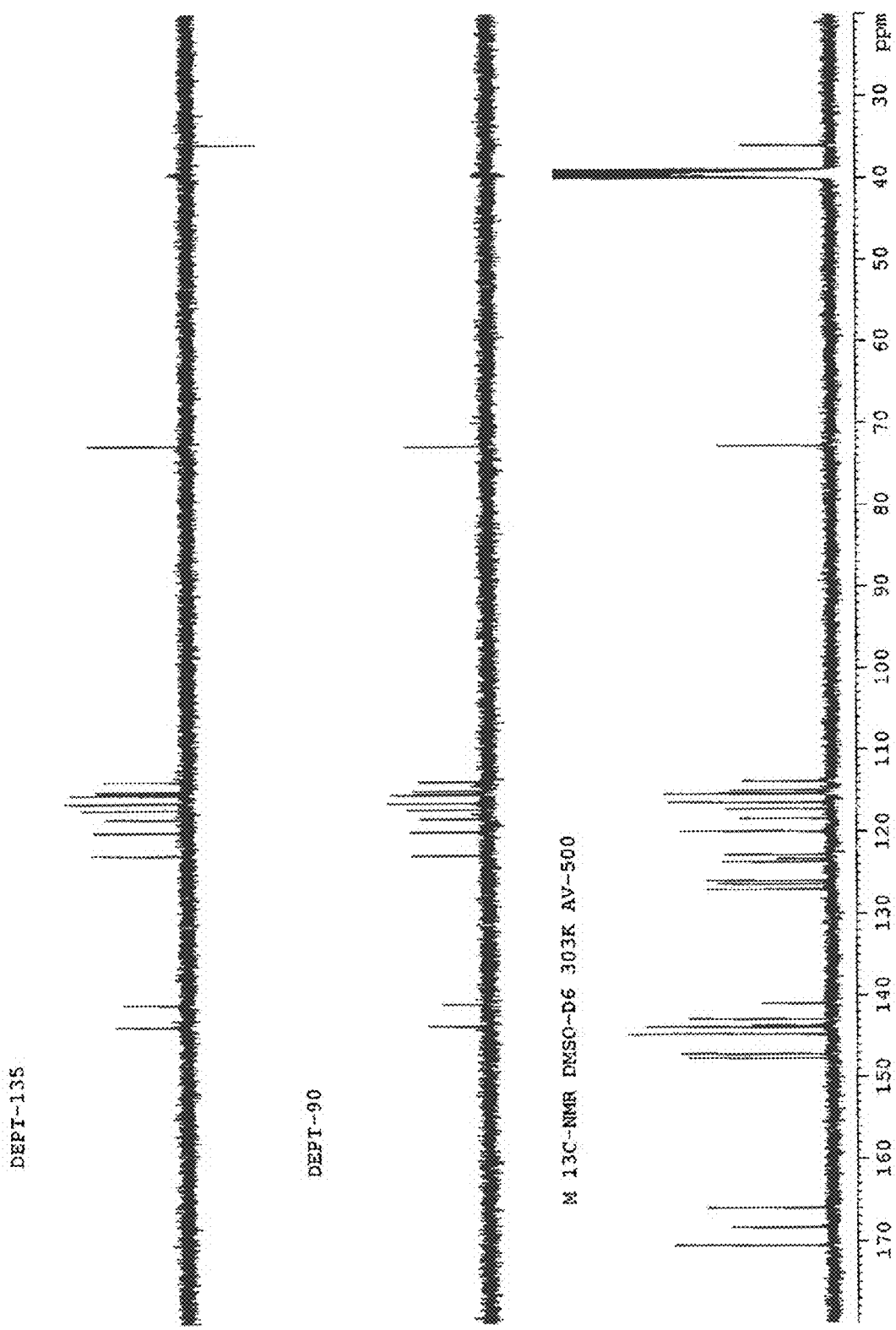
FIG. 4 illustrates the DEPT spectrum of the salvianolic acid T, A: (R)-salvianolic acid T; B: (S)-salvianolic acid T.
Figure 4B:
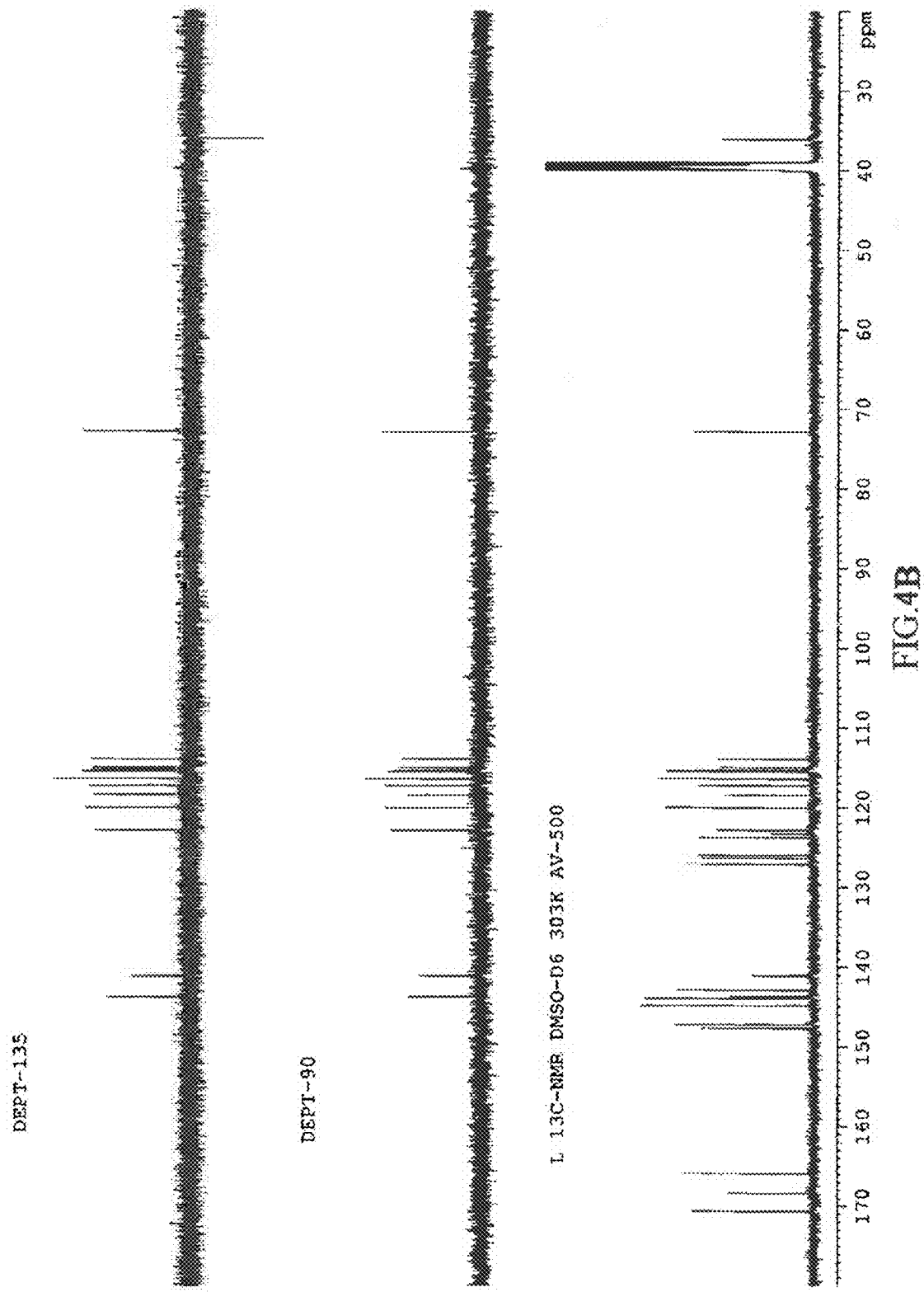
Figure 5A:
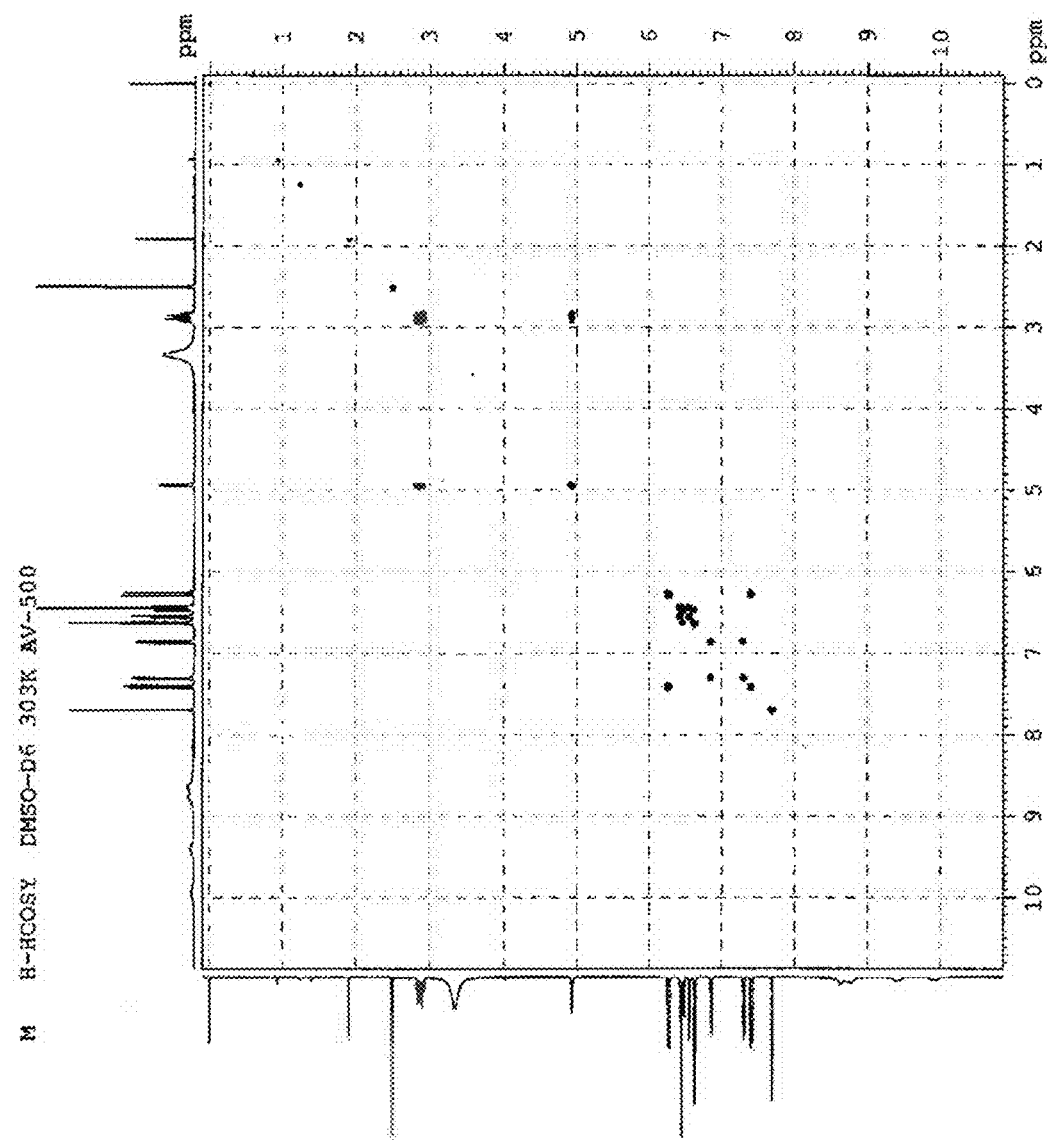
FIG. 5 illustrates the COSY spectrum of the salvianolic acid T, A: (R)-salvianolic acid T; B:(S)-salvianolic acid T.
Figure 5B:
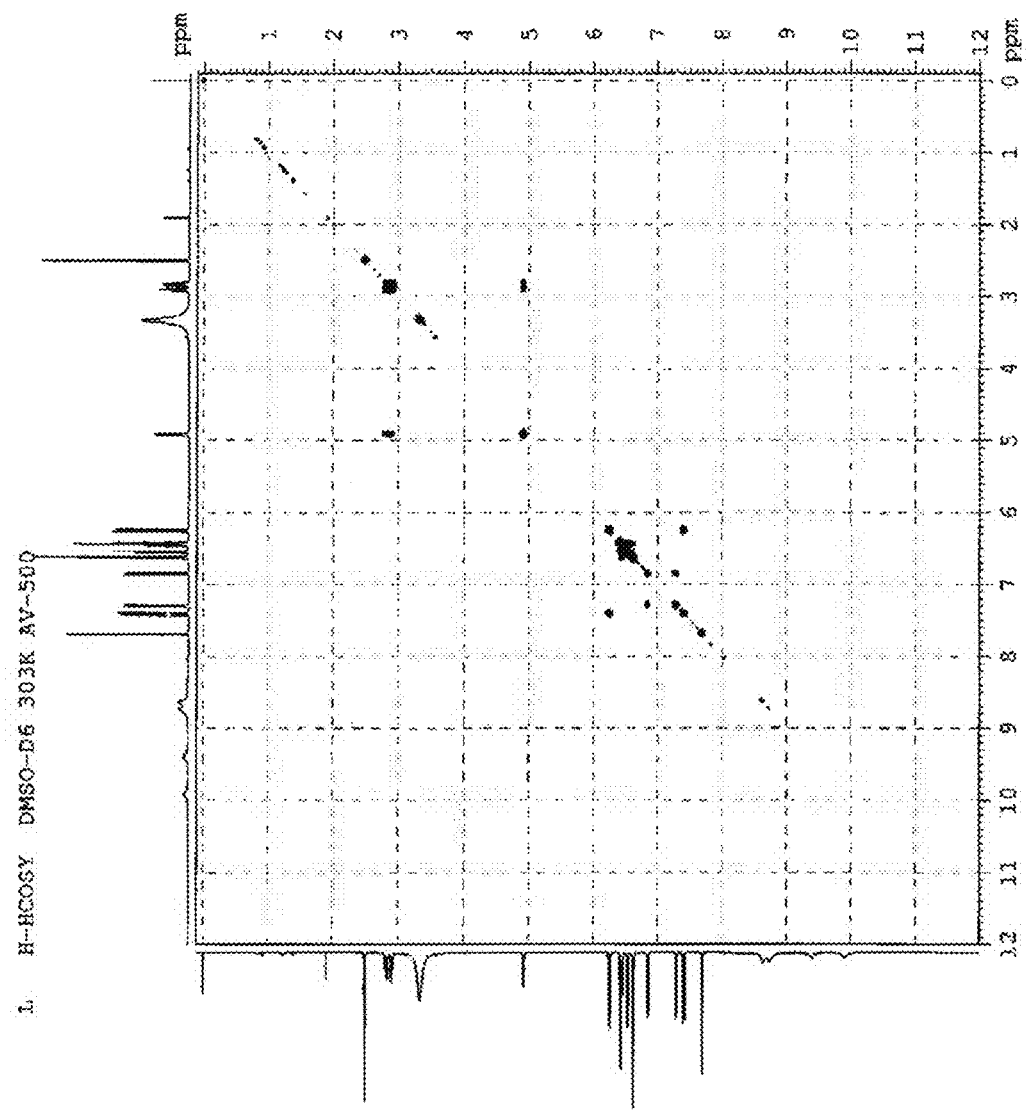
Figure 6A:
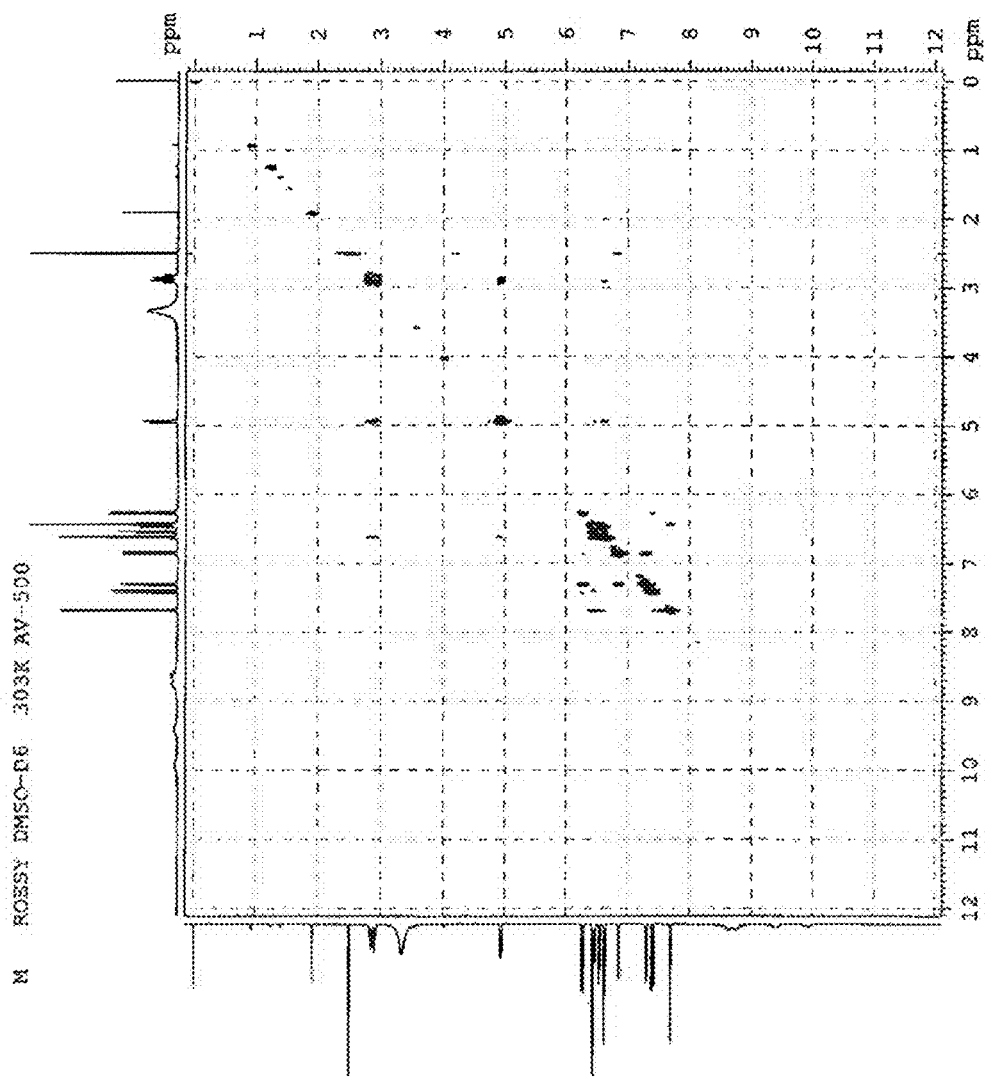
FIG. 6 illustrates the ROESY spectrum of the salvianolic acid T, A: (R)-salvianolic acid T; B: (S)-salvianolic acid T.
Figure 6B:
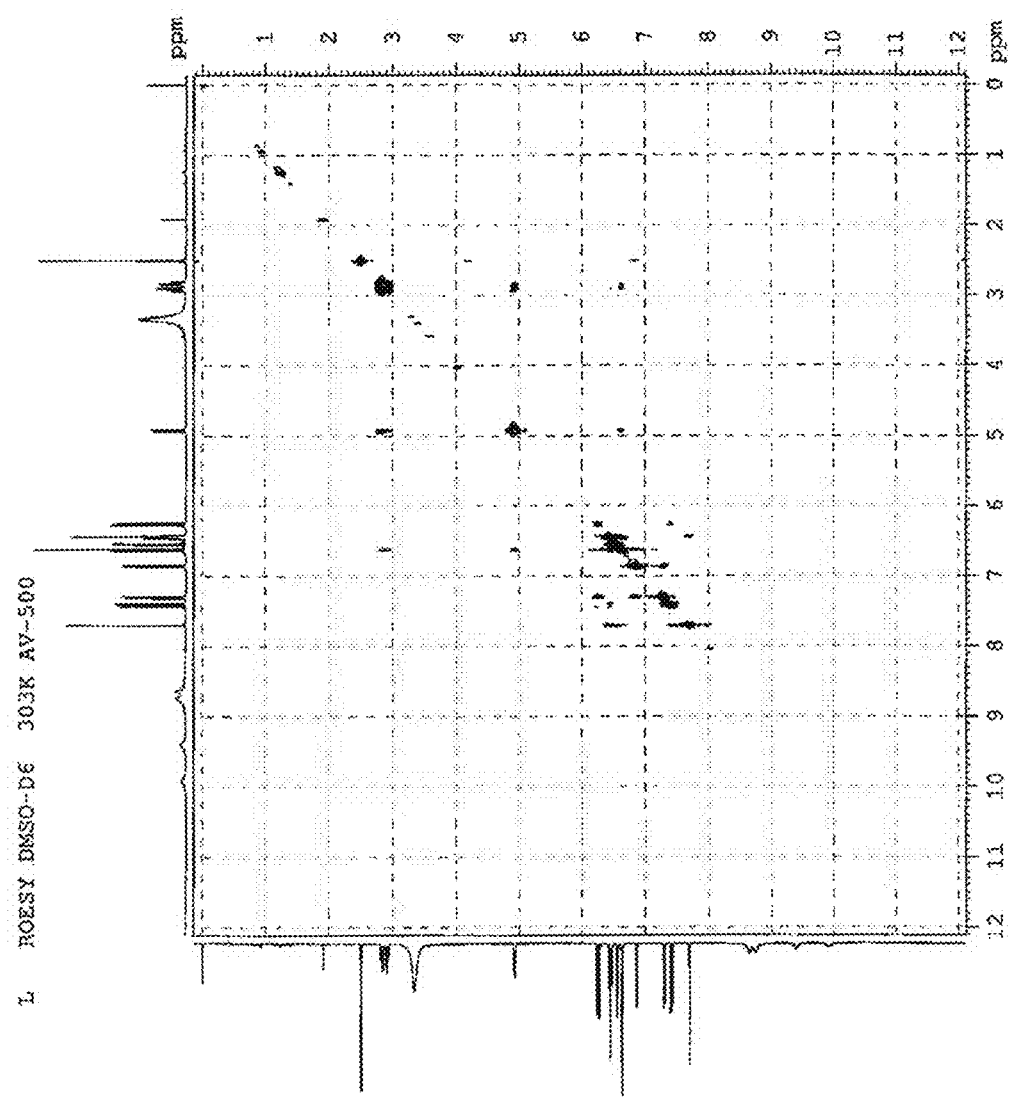
Figure 7A:
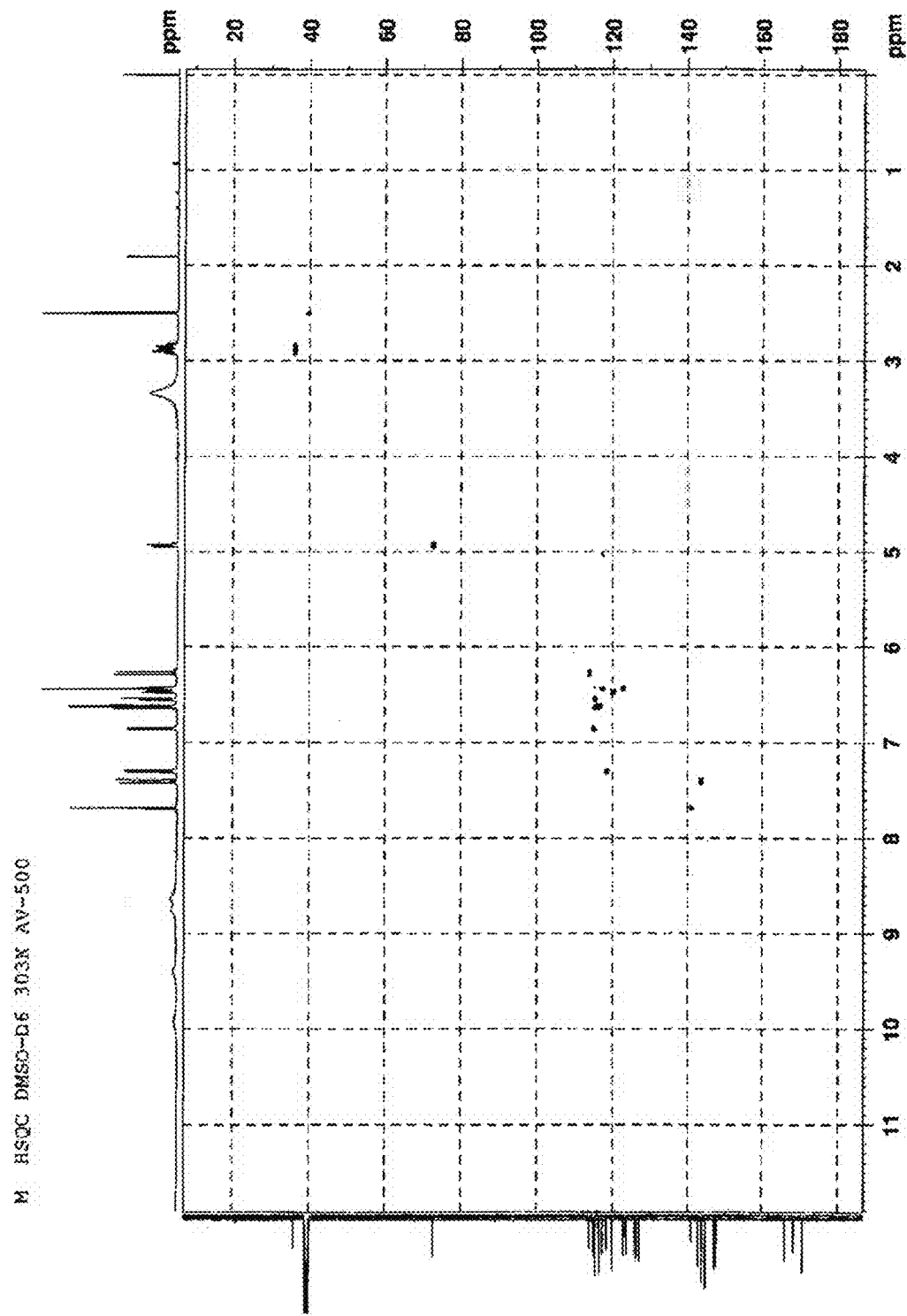
FIG. 7 illustrates the HSQC spectrum of the salvianolic acid T, A: (R)-salvianolic acid T; B: (S)-salvianolic acid T.
Figure 7B:
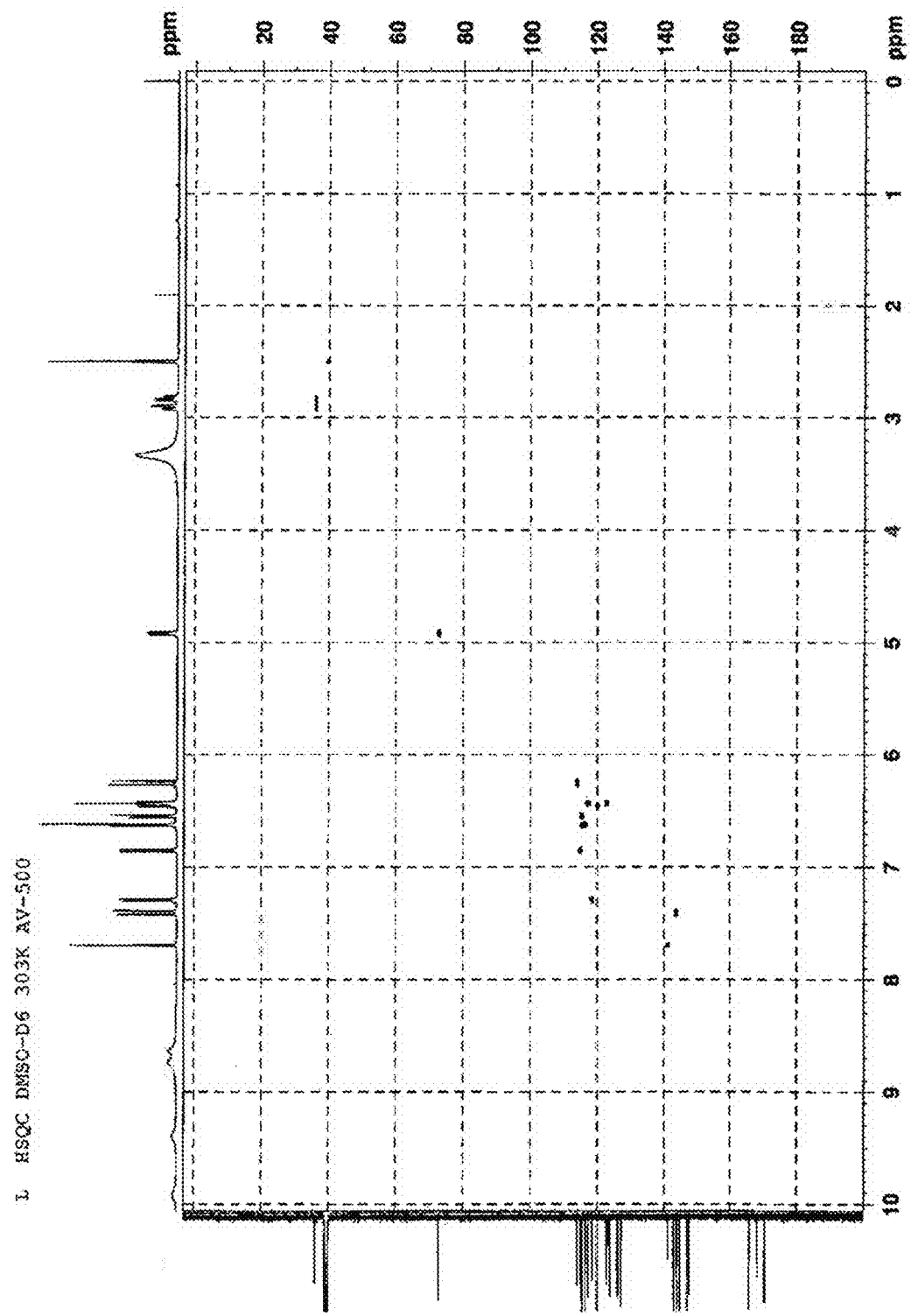
Figure 8A:
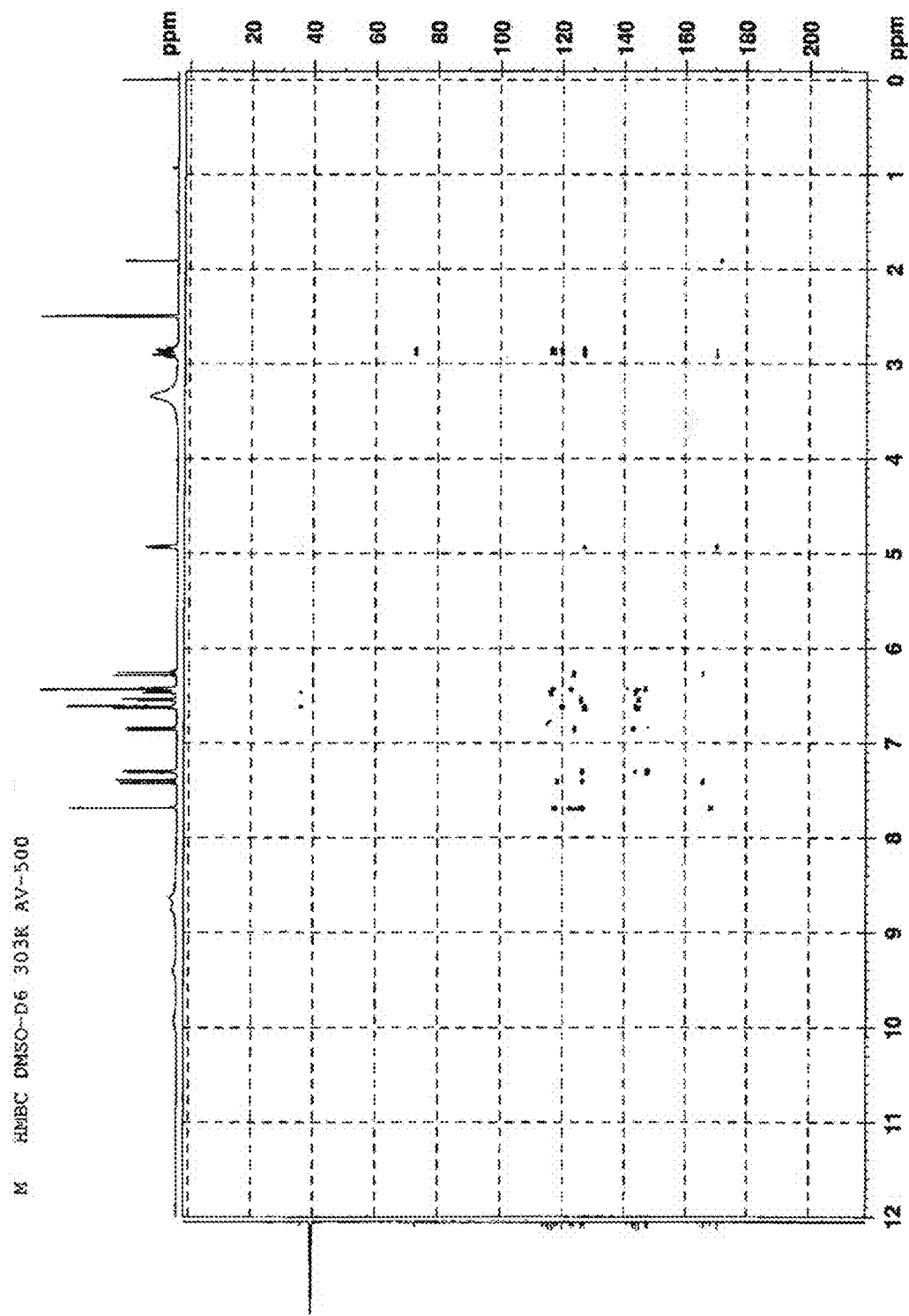
FIG. 8 illustrates the HMBC spectrum of the salvianolic acid T, A: (R)-salvianolic acid T; B:(S)-salvianolic acid T.
Figure 9A:
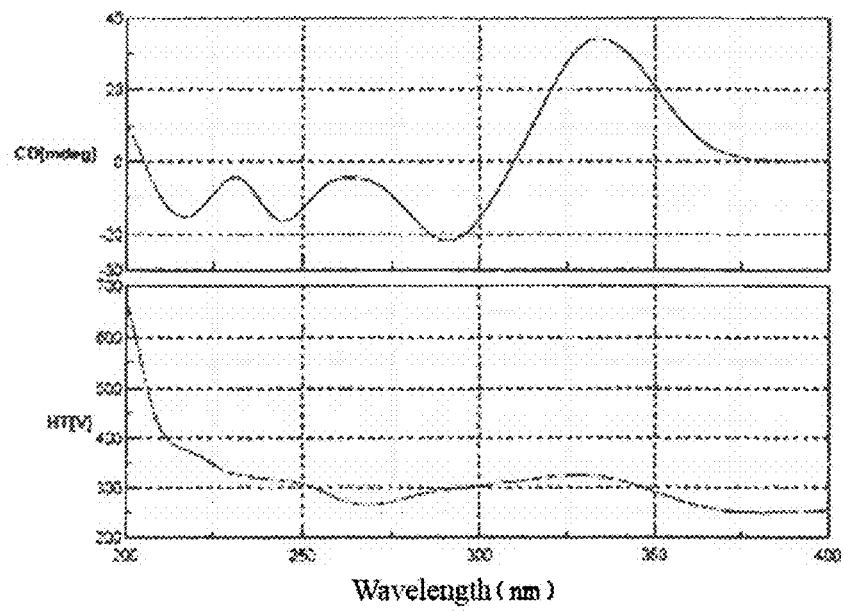
FIG. 9 illustrates the CD spectrum of the salvianolic acid T, A: (R)-salvianolic acid T; B:(S)-salvianolic acid T.
Figure 9B:
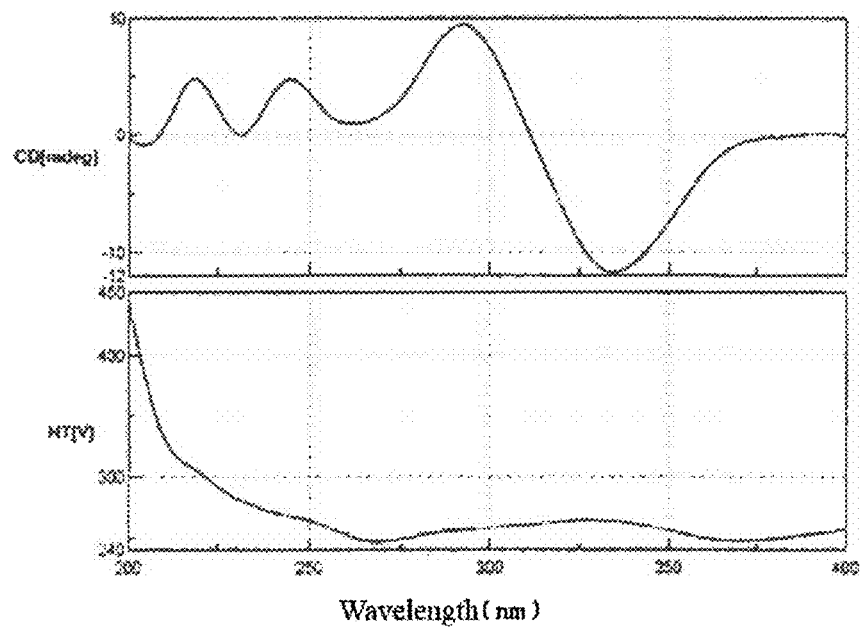
Figure 10A:
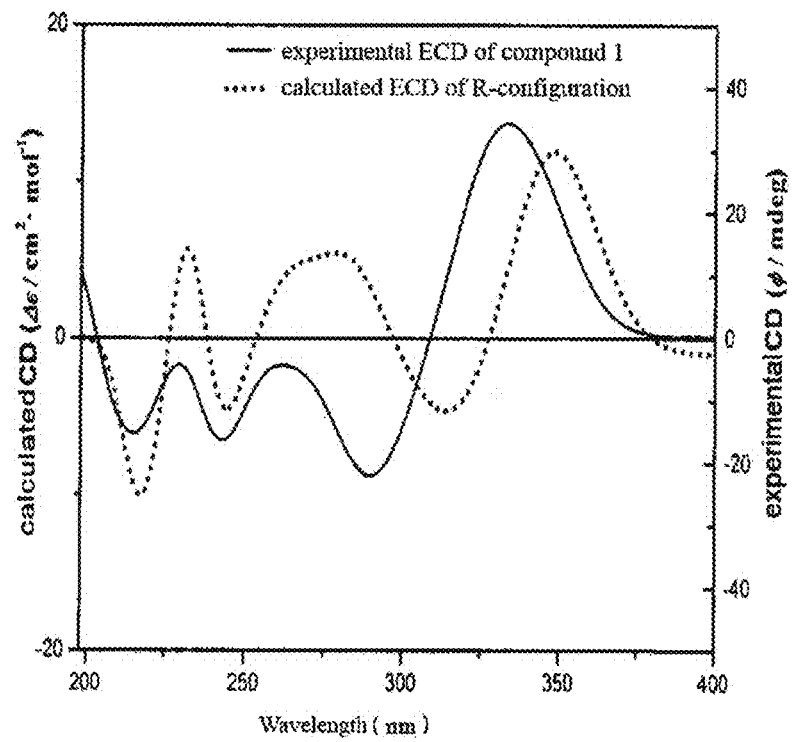
FIG. 10 illustrates the comparison between the CD spectrum and ECD simulated spectrum of the salvianolic acid T, A: (R)-salvianolic acid T; B: (S)-salvianolic acid T.
Figure 10B:
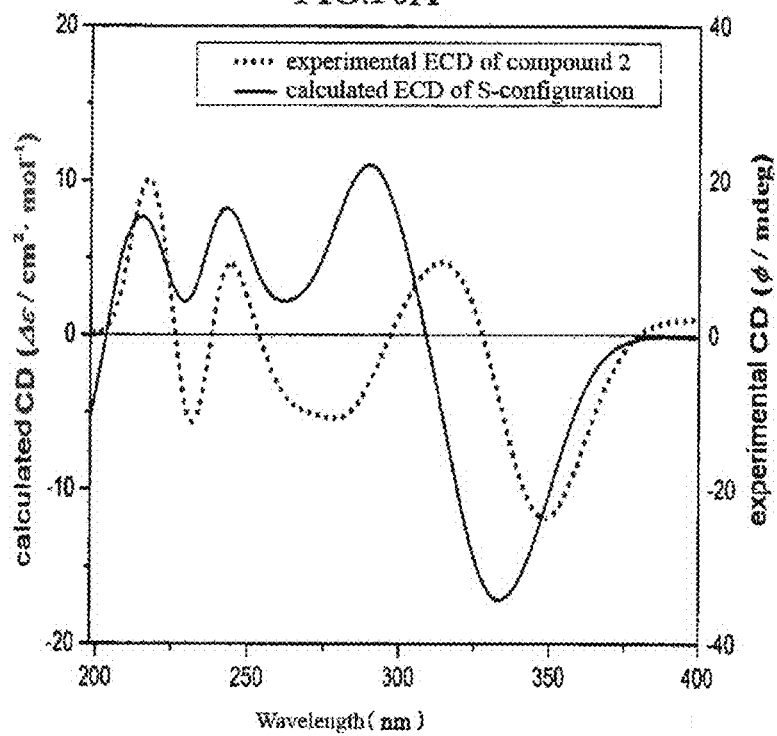

The objective of the present invention is to provide a salvianolic acid compound T of structural formula (I), its pharmaceutically acceptable salts, chiral isomers, solvates and hydrolysable esters.

Structural formula (I)

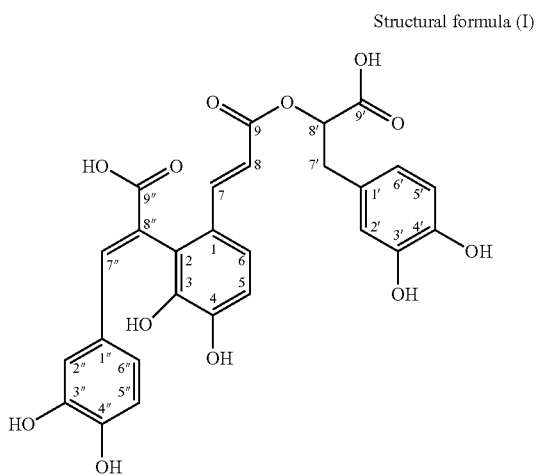 [SMILES: O=C(/C=C/c1ccc(O)c(O)c1/C(=C\c1ccc(O)c(O)c1)C(=O)O)OC(Cc1ccc(O)c(O)c1)C(=O)O]

According to the present invention, the structure of new compound of phenolic acid was identified by physicochemical properties, high resolution mass spectrometry (QFT-ESI), electrospray ionization mass spectrometry (ESI-MS), $^1$H-NMR, $^{13}$C-NMR, DEPT, COSY, HMBC, HMQC and CD (FIG. 1-FIG. 10).

$^1$H-NMR (Hydrogen spectrum) shows 1 signal of methenyl proton attached to oxygen at δ4.93 (1H, dd, 8.0, 4.5 Hz); 11 signals of aromatic proton at δ 6.85 (1H, d, 8.5 Hz), δ 7.31 (1H, d, 8.5 Hz), δ 7.41 (1H, d, 15.5 Hz), δ 6.27 (1H, d, 15.5 Hz), δ 6.62 (1H, s), δ 6.63 (1H, d, 8.0 Hz), δ 6.47 (1H, d, 8.0 Hz), δ 6.44 (1H, d, 2.0 Hz), δ 6.55 (1H, d, 8.5 Hz), δ 6.43 (1H, dd, 8.5, 2.0 Hz), δ 7.69 (1H, s); 2 signals of aliphatic proton at δ 2.89 (2H, ddd, 14.0, 8.0, 4.5 Hz).

$^{13}$C-NMR(Carbon spectrum) shows 27 carbon signals, including 1 aliphatic carbon signal at δ 36.0, 1 signal of methenyl carbon attached to oxygen at δ 72.8, 3 signals of carbonyl carbon at δ 166.0, δ 170.6, δ 168.4, and 22 signals of double-bond carbon at δ 123.7, δ 126.4, δ 142.9, δ 147.7, δ 115.0, δ 118.4, δ 143.7, δ 113.9, δ 127.1, δ 116.5, δ 143.9, δ 144.8, δ 115.5, δ 120.0, δ 126.0, δ 117.3, δ 144.8, δ 147.2, δ 115.3, δ 122.9, δ 141.1, δ 123.4.

The specific rotation of the 2 isomers of the compound in the present invention is −157.5°, 196.6° respectively. The molecular structure of the compound the C-8' absolute configuration of which is determined as S/R configuration is optimized respectively, then the BPV86 method having TD-SCF is used to compute at 6-31++G (2d, p) basis sets, the computing results are read and compared with the CD spectrums of the compound in the present invention, the final results find that the computing results of the compounds of 2 configurations are basically superposing with the experimental CD spectrum diagrams of the compounds in the present invention, concluding the C-8' absolute configurations of the 2 isomers of the compounds in the present invention respectively are S configuration and R configuration (referring to FIG. 10). The main HMBC correlation of the compound in the present invention is as follows:

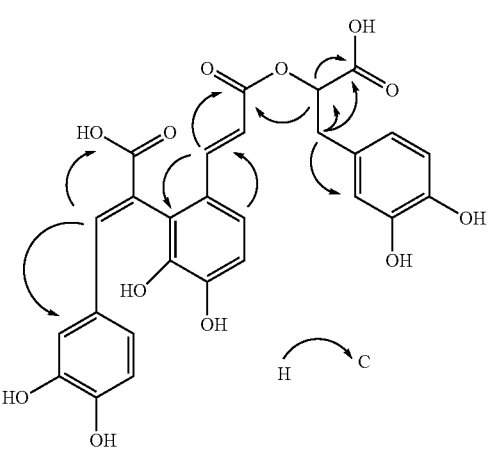

The compound of the present invention is a new compound of salvianolic acid, which is named as the "salvianolic acid T".

Due to the changes of configuration and conformation that occurred in the present compound during the process of extraction, accordingly, changes may take place on its spectral data. But various kinds of isomers produced by configurational and conformational changes will fall within the protection scope of the present invention.

The salvianolic acid T of the present invention, according to the common technical knowledge and the prior art, also can be used in the form of its pharmaceutically acceptable salts or solvates. The pharmaceutically acceptable salts of the salvianolic acid T according to the present invention include conventional and pharmaceutically acceptable salts produced from inorganic or organic base, which are produced by conventional salt-forming method. Suitable examples of the salts include sodium salt, potassium salt, lithium salt, magnesium salt, aluminum salt, calcium salt, zinc salt etc., or salts formed by reacting with N,N'-dibenzyl ethylenediamine, chloroprocaine, choline, diethanolamine, ethylenediamine, N-methyl glucoseimine, procaine and berberine. Before describing the second object of the present invention, the salvianolic acid T described below includes the salvianolic acid T represented by the formula (I) and its pharmaceutically-acceptable salts, chiral isomers, solvates, and hydrolysable esters.

The salvianolic acid T of the present invention is appropriately administered in the form of a pharmaceutical composition, which can be used conventionally by being mixed with one or more kinds of pharmaceutically acceptable carriers or excipients. If possible, the salvianolic acid T of the present invention can be administered as a raw medicine therapeutically, preferably the active components are selected to be directly used as a pharmaceutical preparation. From the viewpoints of compatibility with other components and safety for the patients, the carriers must be pharmaceutically acceptable.

Accordingly, the present invention provides pharmaceutical preparations of the salvianolic acid T, which comprises the salvianolic acid T of the present invention and one or more kinds of pharmaceutically acceptable carriers, with or without other therapeutical and/or preventative components. These preparations can be administered orally, parenterally (including subcutaneously such as injection or reservoir-type tablet, intra-dermally, intrathecally, intramuscularly such as reservoir-type and intravenously), rectally and topically (such as sublingually). The most desirable route of administration, however, depends on the disease of patients. The said pharmaceutical preparations can be a unit preparation, and can be prepared by any method well-known in the pharmaceutical field. All of these methods include the step of combining the salvianolic acid T of the present invention with a carrier constituting one or more kinds of adjuvant components. Generally speaking, said preparations of the present invention are produced as follows: uniformly and compactly combining the salvianolic acid T of the present invention with fluid, or finely crushed solid carries or a mixture of the two, then, if necessary, forming the product into a desired preparation.

Normally, a series of standard pharmaceutical technologies can be used to prepare the pharmaceutical composition of the present invention by utilizing the salvianolic acid T and pharmaceutical carries. The technologies include mixing, granulating and pressing. As well-known to the skilled in the art, the characteristics and forms of the pharmaceutically acceptable carriers or diluents depend on the amount of the active components mixed, administration route and other known factors.

In this application the said pharmaceutically acceptable carriers refer to all sorts of organic or inorganic carriers that can be administered together with the composition, for example, excipient, lubricant, binding agent, disintegrating agent and coating agent used for solid-preparation; or pharmaceutical additives, such as colorant and sweetening-agent. Said pharmaceutical carriers are selected from the group consisting of sugar-alcohol such as mannitol, sorbitol, xylitol; amino acid such as cysteine hydrochloride, methionine, glycine; vitamin C; disodium EDTA, EDTA calcium sodiumsodium pyrosulfite; inorganic salts such as carbonates, acetates, phosphates of monovalent alkali metal or their aqueous solutions; sodium chloride, potassium chloride; sodium metabisulfite, sodium bisulfite, sodium thiosulfate; calcium carbonate, calcium bicarbonate; stearate such as calcium stearate, magnesium stearate; inorganic acid such as hydrochloric acid, acetic acid, sulfuric acid, phosphoric acid; organic acid salts such as sodium lactate; oligosaccharide, polysaccharide, cellulose and derivatives thereof, such as maltose, glucose, fructose, dextran, sucrose, lactose, cyclodextrin (such as β-cyclodextrin), starch; silicon derivatives; alginate; gelatin; polyvinylpyrrolidone; glycerol; agar; surfactant such as Tween-80; polyethyleneglycol; phospholipid materials; kaolin; talc powder etc.

The form of pharmaceutical preparations can be any pharmaceutically acceptable dosage form, including tablets, such as sugar-coated tablets, film-coated tablets and enteric coated tablets; capsules, such as hard capsules and soft capsules; oral solutions; buccal tablets; granules; granules taken after dissolving in boiling water; pills; powders, pastes; pellets, suspensions; pulvis; liquors; injections; suppositories; pastes, such as ointments and plasters; creams; sprays; drops and patches. Preferably, the preparations are in the oral dosage form, such as capsules, tablets, oral solutions, granules, pills, powders, pellets and pastes; and in the form of injections, such as injectable powders, injections and transfusions etc. Most preferably, the preparations are in the form of tablets.

The said oral preparations can contain commonly-used excipient, binding agent, bulking-agent, diluent, tablet-pressing agent, lubricant, disintegrating agent, colorants, flavoring-agent and wetting-agent, and if necessary, the tablets can be coated.

Preferable examples of said excipient include lactose, D-mannitol, D-sorbitol, starch, such as α-starch, dextrin, crystalline cellulose, low-substituted hydroxypropyl cellulose, sodium carboxymethyl cellulose, arabic gum, amylopectin, light anhydrous silicic acid, synthetic aluminum silicate or magnesium aluminum silicate etc.

Preferable examples of said lubricant include magnesium stearate, calcium stearate, talc powder and silica gel etc.

Preferable examples of said binding agent include α-starch, sucrose, gelatin, arabic gum, methylcellulose, carboxymethyl cellulose, sodium carboxymethyl cellulose, crystalline cellulose, sugar, D-mannitol, trehalose, dextrin, amylopectin, hydroxypropyl cellulose, hydroxypropyl methyl cellulose, pyrrolidone etc.

Preferable examples of said disintegrating agent include lactose, sugar, starch, carboxymethyl cellulose, calcium carboxymethyl cellulose, aminoalkyl sodium, sodium carboxymethyl starch, light anhydrous silicic acid, low-substituted hydroxypropyl cellulose etc.

Preferable examples of said coating agent include hydroxypropyl methyl cellulose, hydroxypropyl cellulose, ethyl cellulose, carboxymethyl cellulose, polyvinyl alcohol etc.

Preferable examples of said colorant include water-soluble edible tartrazine dye (food dye such as edible red No. 2 and No. 3, edible yellow No. 4 and No. 5, edible blue No. 1 and No. 2); water-insoluble lake colors (such as aluminum salt of the above-mentioned water-soluble edible tartrazine dye) and natural dye (such as β-carotene, chlorophyll and colcothar) etc.

Preferable examples of said sweetening-agent include saccharin sodium, glycyrrhetinic acid, aspartame and stevioside etc.

Conventional method for preparing tablets comprises combining the salvianolic acid T of the present invention with one or more kinds of pharmaceutically acceptable excipient, and then being pressed or being molded.

The salvianolic acid T of the present invention can also be prepared into oral liquid preparations, for instance, water-soluble or oil-soluble suspensions, solutions, emulsions, syrups, etc. The salvianolic acid T of the present invention can also be prepared into a dry product, re-blended with water or other suitable carriers before use. This sort of liquid preparations can contain conventional additives, including suspending-agent, such as sorbitol syrup, methylcellulose, glucose/syrup, gelatin, hydroxyethyl cellulose, carboxymethyl cellulose, aluminum stearate gel or hydrogenated edible fat; emulsifying-agent, such as lecithin, sorbitan monoleate or arabic gum; non-aqueous carrier (including edible oil), such as almond oil, fractionated coconut oil, butyraceous ester, propylene glycol or ethanol; as well as preservative, such as methylparaben, nipasol, or sorbic acid.

Parenterally-administered preparations include aqueous and non-aqueous sterile injections, wherein these preparations can contain antioxidant, buffering agent, bacteriostatic agent, isotonic agent etc; and aqueous and non-aqueous sterile suspensions, wherein these preparations can contain suspending-agent and thickening agent. The preparations can be preserved in a single-dose or multi-dose vessel such as sealed ampoules and vials, which can be stored under the freeze drying (lyophilization) condition and re-dissolved before use with sterile liquid carrier, such as water for injection.

Rectally-administered preparations can be suppositories containing conventional suppository base, such as cocoa butter, stearic acid or other glycerides or ethylene glycol.

Oral cavity topically-administered preparations, for example the buccally or sublingually administered preparations include troches, wherein the active component is embedded in a flavored base such as sucrose and arabic gum; also pastilles, wherein the active component is embedded in a base such as gelatin and glycerol, or sucrose and arabic gum.

The salvianolic acid T of the present invention can also be prepared into reservoir-type preparations, such a sustained-release preparation can be administered by implantation (such as subcutaneous or intramuscular implantation) or intramuscular injection. Therefore, the salvianolic acid T of the present invention can be prepared with suitable polymers, or hydrophobic materials (such as the emulsion in acceptable oil), or ion-exchange resins, or prepared into a slightly-soluble derivatives, such as slightly-soluble salt.

According to the common technical knowledge and the prior art, the treatment related to the present invention include prevention and treatment for certain diseases or symptoms. Besides, therapeutically effective amount of the salvianolic acid T of the present invention depends on the property of diseases and individual conditions of patients, or follow the physician's advice. Generally, therapeutically effective amount for adult is in a range of 0.02-5000 mg per day, preferably 1-1500 mg per day. The amount can be a single-dosage or multiple-dose that will be taken by patients at appropriate intervals, for example, twice a day, three times a day, four times a day or more. Said preparation of the present invention comprises 0.1-99 wt % of active components, preferably 30-95 wt % for tablets and capsules; and preferably 3-50 wt % for liquid preparations.

On the second object, the present invention relates to the preparation method of the salvianolic acid T, the said method includes the following steps:

(1a) extraction: extracting Radix Salviae Miltiorrhizae crude drug or a mixture of Radix Salviae Miltiorrhizae and other crude drugs with water, concentrating the filtrate to obtain a water extract, then adding alcohol to precipitate and obtain a supernatant, concentrating the supernatant to obtain an alcohol extract;

(1b) separation: diluting the alcohol extract of the step (1a) with water, applying on the macroporous absorbent resin, washing the resin with an acidic aqueous solution to remove impurities and then eluting the resin with ethanol to obtain an ethanol eluent, concentrating the ethanol eluent to obtain an extract;

Or, replacing the above steps (1a) and (1b) by the following step (1):

(1) Synthesis: dissolving salvianolic acid B in the water, heating;

(2) purification: adjusting the pH of the reaction liquid obtained in the step (1) to be acidic or purifying the extract obtained in the step (1b) by the high preparative pressure liquid chromatograph, with C18 reversed phase silica gel column as the chromatographic packing, acetonitrile-water-formic acid as the eluent, carrying out isocratic elution or gradient elution, with a detection wavelength of 280 nm; monitoring the elution process by high performance liquid chromatography, collecting the eluent containing salvianolic acid T; concentrating to obtain the salvianolic acid T.

Further, the present invention relates to a preparation method of the chiral isomers of salvianolic acid T, wherein, the method includes the following steps:

(1a) extraction: extracting Radix Salviae Miltiorrhizae crude drug or a mixture of Radix Salviae Miltiorrhizae and other crude drugs with water, concentrating the filtrate to obtain a water extract, then adding alcohol to precipitate and obtain a supernatant, concentrating the supernatant to obtain an alcohol extract;

(1b) separation: diluting the alcohol extract obtained in the step (1a) with water, applying on the macroporous absorbent resin, washing the resin with an acidic aqueous solution to remove impurities and then eluting the resin with ethanol to obtain an ethanol eluent, concentrating the ethanol eluent to obtain an extract;

Or, replacing the above steps (1a) and (1b) by the following step (1):

(1) Synthesis: dissolving salvianolic acid B in the water, heating;

(2) purification: adjusting the pH of the reaction liquid obtained in the step (1) to be acidic or purifying the extract obtained in the step (1b) by the preparative high pressure liquid chromatograph, with C18 reversed phase silica gel column as the chromatographic packing, acetonitrile-water-formic acid as the eluent, isocratic elution or gradient elution, with a detection wavelength of 280 nm; monitoring the elution process by high performance liquid chromatography, collecting the eluent containing salvianolic acid T; concentrating to obtain the salvianolic acid T.

(3) preparation of the chiral isomers: separating the chiral isomers from the salvianolic acid T obtained in step (2) by preparative liquid chromatograph, with reversed phase chiral column as the chromatographic column, acetonitrile-water-formic acid as the eluent, carrying out isocratic elution or gradient elution, with a detection wavelength of 280 nm; monitoring the elution process by high performance liquid chromatography, collecting the eluent containing (S)-salvianolic acid T and (R)-salvianolic acid T separately, freeze-drying to obtain the pure products of (S)-salvianolic acid T and (R)-salvianolic acid T.

In the said step (1a), the Radix Salviae Miltiorrhizae crude drug or the mixture of Radix Salviae Miltiorrhizae and other crude drugs are decoction pieces, crushed particles or powders, preferably decoction pieces; the said other crude drugs can be the Chinese crude drugs well known to the skilled in the art, which are compatible with Radix Salviae Miltiorrhizae, preferably Radix Notoginseng or Radix Astragali or the combination of the two.

In the said step (1a), the said water-extraction is as follows: decocting the crude drug with water of 4-8 times the volume of the crude drug for 1.5-4 h, preferably for 3 h; filtrating; concentrating the filtrate to obtain a water extract with a relative density of 1.10-1.30 (80□), preferably 1.22 (80□). In order to improve the extraction efficiency and salify the phenolic acid substances, an alkali aqueous solution is used in the said water-extraction step, the said alkali is at least one selected from the group consisting of sodium bicarbonate solution, sodium carbonate aqueous solution, potassium hydrogen carbonate solution, potassium carbonate solution, sodium hydroxide aqueous solution, potassium hydroxide aqueous solution, preferably a sodium bicarbonate aqueous solution in a concentration of 0.3%-0.45% (w/v).

In the step (1a), the said alcohol-precipitation is as follows: adding 95% (v/v) ethanol into the water extract to precipitate until the content of the ethanol being 50%-70% (v/v) (25□), preferably 60% (v/v), and standing still for 8-36 h, preferably 24 h; obtaining the supernatant, recovering ethanol under reduced pressure condition, concentrating to obtain an alcohol extract with a relative density of 1.25-1.5 (60□), preferably an alcohol extract with a relative density of 1.32 (60□). In the step (1b), the said macroporous adsorptive resin is non-polar or weak polar macroporous adsorptive resin, which can be selected from AB-8 type, HPD450 type, D101 type, or X5 type macroporous adsorptive resin, preferably AB-8 type; the weight ratio of the crude drug to the macroporous absorbent resin in the step (1) is 5:1-1:1, preferably 3:1; the said acidic aqueous solution is at least one selected from the group consisting of hydrochloric acid aqueous solution, sulfuric acid aqueous solution, nitric acid aqueous solution and acetic acid aqueous solution or the combination of them, preferably hydrochloric acid aqueous solution; the pH of the solution is adjusted into 1.0-5.0, preferably 3.0; washing with the acidic aqueous solution until the eluent being nearly colorless. Then, 4-10 times of 50%-95% (v/v) ethanol is used to wash the column, preferably 5 times of 95% (v/v) ethanol; the eluent is concentrated to obtain an extract without alcoholic smell.

In the said step (1), the said reaction raw material is salvianolic acid B or its salts.

In the said step (1), the mass ratio of the said salvianolic acid B to the said aqueous solution is 1:0.1-1:100000, preferably 1:200; the reaction temperature is 10-150□, preferably 90□; the reaction time is 10 min to 24 h, preferably 1 h.

In the said step (1), the said aqueous solution can be acidic aqueous solution, neutral aqueous solution or alkaline aqueous solution, preferably alkaline aqueous solution, the said aqueous solution is alkaline aqueous solution, the said alkaline aqueous solution is at least selected from the following aqueous solutions: sodium bicarbonate solution, sodium carbonate aqueous solution, potassium hydrogen carbonate solution, potassium carbonate solution, sodium hydroxide aqueous solution and potassium hydroxide aqueous solution; more preferably, the said alkaline aqueous solution is sodium bicarbonate solution with a concentration of 0.05%-0.45% (w/v).

In the step (2), any one of the hydrochloric acid aqueous solution, sulfuric acid aqueous solution, aqueous solution of nitric acid and acetic acid aqueous solution or combination thereof can be used to adjust the pH of the reaction liquid into 1.0-6.0, preferably, the hydrochloric acid aqueous solution is used to adjust the reaction liquid into 3.0.

In the step (2), the said high pressure liquid chromatograph can be dynamic axial high pressure liquid chromatograph, such as France NOVASEP LC80-600, preferably the chromatographic packing is C18 reversed phase silica gel column (10 μm, YMC Company), dissolving the extract obtained in the said step (1b) with mobile phase (acetonitrile:water:formic acid (volume ratio)=(10:90:1)-(90:10:1)), preferably acetonitrile:water:formic acid (volume ratio)= (10:90:1)-(50:50:1), more preferably acetonitrile:water:formic acid (volume ratio)=15:85:1; the eluent uses the above ratio of the mobile phase, the elution is isocratic elution or gradient elution, preferably isocratic elution with acetonitrile:water:formic acid (volume ratio)=15:85:1; the flow rate is 300 mL/min; the detection wavelength is 280 nm; monitoring the elution process by high performance liquid chromatography, collecting the components the retention time of which is 21.2-24.0 min, concentrating to dry, obtaining salvianolic acid T sample.

In the step (3), Waters Prep 400 preparative liquid chromatograph is used to carry out the chiral isomer separation, the chromatographic column is CHIRALCEL® OD-RH Reversed phase column (250×20 mm, 5 μm), dissolving the salvianolic acid T sample obtained in the step (2) with mobile phase (acetonitrile:water:formic acid (volume ratio)=(10:90:1)-(90:10:1)), preferably acetonitrile:water: formic acid (volume ratio)=15:85:1; the eluent uses the above ratio of the mobile phase, the elution is isocratic elution or gradient elution, preferably isocratic elution with acetonitrile:water:formic acid (volume ratio)=15:85:1; the flow rate is 25 mL/min; the detection wavelength is 280 nm; monitoring the elution process by high performance liquid chromatography, collecting the (S)-salvianolic acid T component with a retention time of 19.5-21.1 min, (R)-salvianolic acid T component with a retention time of 23.9-25.3 min separately, freeze-drying after low temperature (10-40□, preferably 30□) concentration, obtaining (S)-salvianolic acid T pure product and (R)-salvianolic acid T pure product.

The results of the pharmacodynamic test in the present invention showed that, the salvianolic acid T of the present invention had the activity of preventing acute myocardial infarction and acute myocardial ischemia, excellent free radical scavenging and reducing capacity, as well as the activity of treating pulmonary fibrosis.

Therefore, the present invention also relates to the following:

Antioxidant, free radical scavenger comprising the salvianolic acid T, its pharmaceutically acceptable salts, chiral isomers, solvates and hydrolysable esters.

A use of the salvianolic acid T, its pharmaceutically acceptable salts, chiral isomers, solvates and hydrolysable esters in preparing drugs for treating acute myocardial infarction and acute myocardial ischemia.

A use of the salvianolic acid T, its pharmaceutically acceptable salts, chiral isomers, solvates and hydrolysable esters in preparing drugs for treating pulmonary fibrosis disease.

A use of the salvianolic acid T, its pharmaceutically acceptable salts, chiral isomers, solvates and hydrolysable esters in preparing antioxidants.

Using the salvianolic acid T, its pharmaceutically acceptable salts, chiral isomers, solvates and hydrolysable esters for treating acute myocardial infarction, acute myocardial ischemia or pulmonary fibrosis disease.

Using the salvianolic acid T, its pharmaceutically acceptable salts, chiral isomers, solvates and hydrolysable esters for delaying senility.

Using the salvianolic acid T, its pharmaceutically acceptable salts, chiral isomers, solvates and hydrolysable esters described in [1] for antioxidation.

EXAMPLES

The technical proposals of the present invention are further illustrated by the following preparation examples and experimental examples. But it should be understood that, the protection scope of the present invention should not be limited to these preparation examples and experimental examples.

Preparation Example 1 Preparation of the Salvianolic Acid T, (S)-Salvianolic Acid T, (R)-Salvianolic Acid T

*Salvia miltiorrhiza* decoction pieces were placed in a Chinese medicine decocting device, water containing 0.3% (w/v) sodium bicarbonate of 6 times the quality of the *Salvia miltiorrhiza* decoction pieces was added, decocted for 2 h, filtered, the filtrate was concentrated to obtain a water extract with a relative density of 1.22 (80□).

A 95% (v/v) ethanol was added into the above extract to perform precipitation until the final ethanol content being 60% (v/v) (25□), standing still for 24 h; the supernatant was obtained and concentrated under reduced pressure condition to obtain an ethanol extract with a relative density of 1.37 (60° C.).

The above ethanol extract was dissolved with water, and then applied on AB-8 macroporous absorbent resin column, the acidic aqueous solution with pH-value of 3.0 was used to wash the column until the eluent became nearly colorless, then, 95% (v/v) ethanol having a volume of 5 times of the column was used to elute, the eluent was concentrated to obtain an extract without alcoholic smell.

The extract obtained in the previous step was dissolved with mobile phase (acetonitrile:water:formic acid (volume ratio)=15:85:1), France NOVASEP LC80-600 dynamic axial high pressure liquid chromatograph was used for purification, the chromatographic packing was C18 reversed phase silica gel column (10 μm, YMC Company), acetonitrile:water:formic acid (volume ratio)=15:85:1 was used for isocratic elution; the flow rate was 300 mL/min; the detection wavelength was 280 nm. Monitoring the elution process by high performance liquid chromatography, collecting the components the retention time of which is 21.2-24.0 min, concentrating to dry by rotary evaporator, obtaining salvianolic acid T sample.

The above salvianolic acid T sample was dissolved with mobile phase (acetonitrile:water:formic acid (volume ratio)=17:83:1), preparative liquid chromatograph was used for chiral isomer separation, the chromatographic column was CHIRALCEL® OD-RH reversed phase column (250× 20 mm, 5 μm), acetonitrile:water:formic acid (volume ratio)=17:83:1 was used for isocratic elution; the flow rate was 25 mL/min; the detection wavelength was 280 nm. Monitoring the elution process by high performance liquid chromatography, collecting the (S)-salvianolic acid T component with a retention time of 19.5-21.1 min, (R)-salvianolic acid T component with a retention time of 23.9-25.3 min, concentrating the eluent by rotary evaporator at 30□, then, freeze-drying to obtain (S)-salvianolic acid T pure product and (R)-salvianolic acid T pure product.

The quasi-molecular ion peak of (S)-salvianolic acid T provided by the high-resolution mass spectrometry was m/z=537.1033; the quasi-molecular ion peak of (R)-salvianolic acid T was [M-H]− m/z 537.1034.

The attribution of the nuclear magnetic resonance spectra data of (S)-salvianolic acid T and (R)-salvianolic acid T was showed in the following table:

TABLE 1

The nuclear magnetic resonance spectra data of (R)-salvianolic acid T (DMSO, J Hz)

| Number | $\delta_H$ | $\delta_C$ | $^1H$-$^1H$ COSY | HMBC |
|---|---|---|---|---|
| 1 | — | 123.7 | | H-5, H-8 |
| 2 | — | 126.4 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.31 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 113.9 | H-7 | H-7 |
| 9 | — | 166.0 | | H-7, H-8, H-8' |
| 1' | — | 127.1 | | H-2', H-5', H-8' H-7' |
| 2' | 6.62 (1H, s) | 116.5 | H-6' | H-6' |
| 3' | — | 143.9 | | H-2', H-5' |
| 4' | — | 144.8 | | H-2', H-5', H-6' |
| 5' | 6.63 (1H, d, 8.0 Hz) | 115.5 | H-6' | H-6' |
| 6' | 6.47 (1H, d, 8.0 Hz) | 120.0 | H-2', 5' | H-2', H-5' |
| 7' | 2.89 (2H, ddd, 14.0, 8.0, 4.5 Hz) | 36.0 | H-8' | H-2', H-5', H-6', H-8' |
| 8' | 4.93 (1H, dd, 8.0, 4.5 Hz) | 72.8 | H-7' | H-7' |
| 9' | — | 170.6 | | H-7', H-8' |
| 1" | — | 126.0 | | H-2" |
| 2" | 6.44 (1H, d, 2.0 Hz) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 8.5 Hz) | 115.3 | H-6" | |
| 6" | 6.43 (1H, dd, 8.5, 2.0 Hz) | 122.9 | H-2", 5" | H-2", H-7" |
| 7" | 7.69 (1H, s) | 141.1 | | H-6" |
| 8" | — | 123.4 | | H-7" |
| 9" | — | 168.4 | | H-7" |

TABLE 2

The nuclear magnetic resonance spectra data of (S)-salvianolic acid T(DMSO, J Hz)

| Number | $\delta_H$ | $\delta_C$ | $^1H$-$^1H$ COSY | HMBC |
|---|---|---|---|---|
| 1 | — | 123.8 | | H-5, H-8 |
| 2 | — | 126.3 | | H-6, H-7, H-7" |
| 3 | — | 142.9 | | H-5 |
| 4 | — | 147.7 | | H-5, H-6 |
| 5 | 6.85 (1H, d, 8.5 Hz) | 115.0 | H-6 | |
| 6 | 7.29 (1H, d, 8.5 Hz) | 118.4 | H-5 | H-7 |
| 7 | 7.41 (1H, d, 15.5 Hz) | 143.7 | H-8 | H-6 |
| 8 | 6.27 (1H, d, 15.5 Hz) | 114.0 | H-7 | H-7 |
| 9 | — | 165.9 | | H-7, H-8, H-8' |
| 1' | — | 127.2 | | H-2', H-5', H-8', H-7' |
| 2' | 6.62 (1H, s) | 116.5 | H-6' | H-6', H-7' |
| 3' | — | 143.9 | | H-2', H-5', H-6' |
| 4' | — | 144.9 | | H-2', H-5' |

TABLE 2-continued

The nuclear magnetic resonance spectra data of (S)-salvianolic acid T(DMSO, J Hz)

| Number | $\delta_H$ | $\delta c$ | $^1H\text{-}^1H$ COSY | HMBC |
|---|---|---|---|---|
| 5' | 6.63 (1H, d, 8.0 Hz) | 115.5 | H-6' | |
| 6' | 6.45 (1H, d, 8.0 Hz) | 120.1 | H-2', 5' | H-2', H-5', H-7' |
| 7' | 2.87 (2H, ddd, 14.0, 8,0, 4.0 Hz) | 36.1 | H-8' | H-2', H-5', H-6' H-8' |
| 8' | 4.92 (1H, dd, 8.0, 4.0 Hz) | 72.9 | H-7' | H-7' |
| 9' | — | 170.6 | | H-7', H-8' |
| 1" | — | 126.0 | | H-5" |
| 2" | 6.43 (1H, d, 2.0) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 9.0) | 115.3 | H-6" | |
| 6" | 6.43 (1H, dd, 8.5, 2.0) | 122.9 | H-2", 5" | H-2", H-7" |
| 7" | 7.69 (1H, s) | 141.1 | | H-2", H-6" |
| 8" | — | 123.3 | | |
| 9" | — | 168.4 | | H-7" |

Preparation Example 2 Preparation Of Salvianolic Acid T, (S)-Salvianolic Acid T, (R)-Salvianolic Acid T

*Salvia* miltiorrhiza and Radix Notoginseng decoction pieces were placed in a Chinese medicine decocting device, water containing 0.45% (w/v) sodium bicarbonate of 4 times the volume of the *Salvia* miltiorrhiza and Radix Notoginseng decoction pieces was added, decocted for 2 h, filtered, the filtrate was concentrated to obtain a water extract with a relative density of 1.25 (80□).

A 95% (v/v) ethanol was added into the above water extract to perform precipitation until the final ethanol content being 65% (v/v) (25□), standing still for 12 h; the supernatant was obtained and concentrated under reduced pressure condition to obtain an ethanol extract with a relative density of 1.28 (60° C.).

The above ethanol extract was dissolved with water, and then applied on AB-8 macroporous absorbent resin column, the acidic aqueous solution with pH-value of 2.5 was used to wash the column until the eluent became nearly colorless, then, 95% (v/v) ethanol having a volume of 4 times of the column was used to elute, the eluent was concentrated to obtain an extract without alcoholic smell.

The extract obtained in the previous step was dissolved with mobile phase (acetonitrile:water:formic acid (volume ratio)=15:85:1), France NOVASEP LC80-600 dynamic axial high pressure liquid chromatograph was used for purification, the chromatographic packing was C18 reversed phase silica gel (10 μm, YMC Company), the following conditions were used for linear gradient elution:acetonitrile:water:formic acid (volume ratio) was changed from 15:85:1 to 20:80:1 from 0 min to 60 min; flow rate: 300 mL/min; detection wavelength: 280 nm. Monitoring the elution process by high performance liquid chromatography, collecting the components the retention time of which was 29.5-32.1 min, concentrating to dry by rotary evaporator, obtaining salvianolic acid T sample.

The above salvianolic acid T sample was dissolved with mobile phase (acetonitrile:water:formic acid (volume ratio)=17:83:1), Waters Prep 400 preparative liquid chromatograph was used for chiral isomer separation, the chromatographic column was CHIRALCEL® OD-RH Reversed phase column (250×20 mm, 5 μm), the following conditions were used for linear gradient elution:acetonitrile:water:formic acid (volume ratio) was linearly changed from 17:83:1 to 22:78:1 from 0 min to 45 min; the flow rate:20 mL/min; the detection wavelength: 280 nm. Monitoring the elution process by high performance liquid chromatography, collecting the (S)-salvianolic acid T component with a retention time of 25.2-27.1 min, (R)-salvianolic acid T component with a retention time of 32.4-34.2 min, concentrating the eluent by rotary evaporator at 30□, then, freeze-drying to obtain (S)-salvianolic acid T pure product and (R)-salvianolic acid T pure product.

The quasi-molecular ion peak of (S)-salvianolic acid T provided by the high-resolution mass Spectrometry was m/z=537.1035; the quasi-molecular ion peak of (R)-salvianolic acid T was [M-H]- m/z 537.1034.

The attribution of the nuclear magnetic resonance spectra data of (S)-salvianolic acid T and (R)-salvianolic acid T were showed in the following table:

TABLE 3

The nuclear magnetic resonance spectra data of (S)-salvianolic acid T (DMSO, J Hz)

| Number | $\delta_H$ | $\delta c$ | $^1H\text{-}^1H$ COSY | HMBC |
|---|---|---|---|---|
| 1 | — | 123.8 | | H-5, H-8 |
| 2 | — | 126.3 | | H-6, H-7, H-7" |
| 3 | — | 142.9 | | H-5 |
| 4 | — | 147.7 | | H-5, H-6 |
| 5 | 6.85 (1H, d, 8.5) | 115.0 | H-6 | |
| 6 | 7.29 (1H, d, 8.5) | 118.4 | H-5 | H-7 |
| 7 | 7.41 (1H, d, 15.5) | 143.7 | H-8 | H-6 |
| 8 | 6.27 (1H, d, 15.5) | 114.0 | H-7 | H-7 |
| 9 | — | 165.9 | | H-7, H-8, H-8' |
| 1' | — | 127.2 | | H-2', H-5', H-8', H-7' |
| 2' | 6.62 (1H, s) | 116.5 | H-6' | H-6', H-7' |
| 3' | — | 143.9 | | H-2', H-5', H-6' |
| 4' | — | 144.9 | | H-2', H-5' |
| 5' | 6.63 (1H, d, 8.0) | 115.5 | H-6' | |
| 6' | 6.45 (1H, d, 8.0) | 120.1 | H-2', 5' | H-2', H-5', H-7' |
| 7' | 2.87 (2H, ddd, 14.0, 8.0, 4.0) | 36.1 | H-8' | H-2', H-5', H-6', H-8' |
| 8' | 4.92 (1H, dd, 8.0, 4.0) | 72.9 | H-7' | H-7' |
| 9' | — | 170.6 | | H-7', H-8' |
| 1" | — | 126.0 | | H-5" |
| 2" | 6.43 (1H, d, 2.0) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 9.0) | 115.3 | H-6" | |
| 6" | 6.43 (1H, dd, 8.5, 2.0) | 122.9 | H-2", 5" | H-2", H-7" |
| 7" | 7.69 (1H, s) | 141.1 | | H-2", H-6" |
| 8" | — | 123.3 | | |
| 9" | — | 168.4 | | H-7" |

TABLE 4

The nuclear magnetic resonance spectra data of (R)-salvianolic acid T (DMSO, J Hz)

| Number | $\delta_H$ | $\delta c$ | $^1H\text{-}^1H$ COSY | HMBC |
|---|---|---|---|---|
| 1 | — | 123.7 | | H-5, H-8 |
| 2 | — | 126.4 | | H-6, H-7, H-7" |
| 3 | — | 142.9 | | H-5 |
| 4 | — | 147.7 | | H-5, H-6 |
| 5 | 6.85 (1H, d, 8.5) | 115.0 | H-6 | |
| 6 | 7.31 (1H, d, 8.5) | 118.4 | H-5 | H-7 |
| 7 | 7.41 (1H, d, 15.5) | 143.7 | H-8 | H-6 |
| 8 | 6.27 (1H, d, 15.5) | 113.9 | H-7 | H-7 |
| 9 | — | 166.0 | | H-7, H-8, H-8' |
| 1' | — | 127.1 | | H-2', H-5', H-8', H-7' |

TABLE 4-continued

The nuclear magnetic resonance spectra data of
(R)-salvianolic acid T (DMSO, J Hz)

| Number | $\delta_H$ | $\delta_C$ | $^1H$-$^1H$ COSY | HMBC |
|---|---|---|---|---|
| 2' | 6.62 (1H, s) | 116.5 | H-6' | H-6' |
| 3' | — | 143.9 | | H-2', H-5' |
| 4' | — | 144.8 | | H-2', H-5', H-6' |
| 5' | 6.63 (1H, d, 8.0) | 115.5 | H-6' | H-6' |
| 6' | 6.47 (1H, d, 8.0) | 120.0 | H-2', 5' | H-2', H-5' |
| 7' | 2.89 (2H, ddd, 14.0, 8.0, 4.5) | 36.0 | H-8' | H-2', H-5', H-6', H-8' |
| 8' | 4.93 (1H, dd, 8.0, 4.5) | 72.8 | H-7' | H-7' |
| 9' | — | 170.6 | | H-7', H-8' |
| 1" | — | 126.0 | | H-2" |
| 2" | 6.44 (1H, d, 2.0) | 117.3 | H-6" | H-6", H-7" |
| 3" | — | 144.8 | | H-2", H-5" |
| 4" | — | 147.2 | | H-2", H-5", H-6" |
| 5" | 6.55 (1H, d, 8.5) | 115.3 | H-6" | |
| 6" | 6.43 (1H, dd, 8.5, 2.0) | 122.9 | H-2", 5" | H-2", H-7" |
| 7" | 7.69 (1H, s) | 141.1 | | H-6" |
| 8" | — | 123.4 | | H-7" |
| 9" | — | 168.4 | | H-7" |

Preparation Example 3 Preparation of Salvianolic Acid T, (S)-Salvianolic Acid T, (R)-Salvianolic Acid T Salvianolic acid B was taken and dissolved in water containing 0.3% (w/v) sodium bicarbonate of 200 times (mass ratio) salvianolic acid B, placed in round-bottom flask, refluxing for 1 h at 90□.

After the reaction, hydrochloric acid aqueous solution of 0.1 mol/L was used to adjust the pH to 3.0, then dissolved with mobile phase (acetonitrile:water:formic acid (volume ratio)=15:85:1), France NOVASEP LC80-600 dynamic axial high pressure liquid chromatograph was used for purification, the chromatographic packing was C18 reversed phase silica gel (10 μm, YMC Company), acetonitrile:water:formic acid (volume ratio)=15:85:1 was used for isocratic elution; acetonitrile:water:formic acid (volume ratio) was changed from 15:85:1 to 20:80:1 from 0 min to 60 min; the flow rate was 300 mL/min; the detection wavelength was 280 nm. Monitoring the elution process by high performance liquid chromatography, collecting the components the retention time of which was 21.2-24.0 min, concentrating to dry by rotary evaporator, obtaining salvianolic acid T sample.

The above salvianolic acid T sample was dissolved with mobile phase (acetonitrile:water:formic acid (volume ratio)=17:83:1), Waters Prep 400 preparative liquid chromatograph was used for chiral isomer separation, the chromatographic column was CHIRALCEL® OD-RH reversed phase column (250×20 mm, 5 μm), acetonitrile:water:formic acid (volume ratio)=17:83:1 was used for isocratic elution; the flow rate was 25 mL/min; the detection wavelength was 280 nm. Monitoring the elution process by high performance liquid chromatography, collecting the (S)-salvianolic acid T component with a retention time of 19.5-21.1 min, (R)-salvianolic acid T component with a retention time of 23.9-25.3 min, concentrating the eluent by rotary evaporator at 30□, then, freeze-drying to obtain (S)-salvianolic acid T pure product and (R)-salvianolic acid T pure product.

Preparation Example 4 Preparation of Salvianolic Acid T, (S)-Salvianolic Acid T, (R)-Salvianolic Acid T Magnesium salvianolic acid B salt was taken and dissolved in water containing 0.05% sodium bicarbonate of 300 times (mass ratio) magnesium salvianolic acid B salt, placed in round-bottom flask, refluxing for 2 h at 90□.

After the reaction, hydrochloric acid aqueous solution of 0.1 mol/L was used to adjust the pH to 3.0, then dissolved with mobile phase (acetonitrile:water:formic acid (volume ratio)=15:85:1), France NOVASEP LC80-600 dynamic axial high pressure liquid chromatograph was used for purification, the chromatographic packing was C18 reversed phase silica gel (10 μm, YMC Company), the following conditions were used for linear gradient elution: acetonitrile:water:formic acid (volume ratio) was changed from 15:85:1 to 20:80:1 from 0 min to 60 min; flow rate: 250 mL/min; detection wavelength: 280 nm. Monitoring the elution process by high performance liquid chromatography, collecting the components the retention time of which was 29.5-32.1 min, concentrating to dry by rotary evaporator, obtaining salvianolic acid T sample.

The above salvianolic acid T sample was dissolved with mobile phase (acetonitrile:water:formic acid (volume ratio)=17:83:1), Waters Prep 400 preparative liquid chromatograph was used for chiral isomer separation, the chromatographic column was CHIRALCEL® OD-RH Reversed phase column (250×20 mm, 5 μm), the following conditions were used for linear gradient elution:acetonitrile:water:formic acid (volume ratio) was linearly changed from 17:83:1 to 22:78:1 from 0 min to 45 min; flow rate: 20 mL/min; detection wavelength: 280 nm. Monitoring the elution process by high performance liquid chromatography, collecting the (S)-salvianolic acid T component with a retention time of 25.2-27.1 min, (R)-salvianolic acid T component with a retention time of 32.4-34.2 min, concentrating the eluent by rotary evaporator at 30□, then, freeze-drying to obtain (S)-salvianolic acid T pure product and (R)-salvianolic acid T pure product.

Formulation Example 1 Preparation Tablets of Salvianolic Acid T, (S)-Salvianolic Acid T, (R)-Salvianolic Acid T Formulation:

| | |
|---|---|
| Salvianolic acid T, (S)-salvianolic acid T, (R)-salvianolic acid T | 100 g |
| Avicel | 50 g |
| Lactose | 30 g |
| Starch | 55 g |
| Sodium carboxymethyl starch | 10 g |
| 5% (w/v) PVP anhydrous ethanol | proper amount |
| Magnesium stearate | 5 g |

The above formulation was prepared into 1000 tablets.

Preparation Process:

1. Granulation

The salvianolic acid T, (S)-salvianolic acid T, (R)-salvianolic acid T and other adjuvants listed in the formulation were sieved through a 100-mesh sieve, respectively. According to the formulation dosage, the salvianolic acid T, avicel, starch and sodium carboxymethyl starch were well blended according to equivalent progressively increasing method, a proper amount of 5% (w/v) PVP anhydrous ethanol was used to produce the soft materials, granulated with a 14-mesh sieve and dried at 50-60□ for 1 h. The magnesium stearate according to the formulation dosage was added to sieve the granule with 14-mesh sieve.

2. Tablet Pressing

The resulting granule was pressed with a punch die to prepare the tablets.

Formulation Example 2 Preparation Capsules of Salvianolic Acid T, (S)-Salvianolic Acid T, (R)-Salvianolic Acid T Formulation:

| Salvianolic acid T, (S)-salvianolic acid T, (R)-salvianolic acid T | 100 g |
| --- | --- |
| Starch | 200 g |
| Sodium carboxymethyl starch | 15 g |
| 5% (w/v) PVP anhydrous ethanol | proper amount |
| Magnesium stearate | 5 g |

The above formulation was prepared into 1000 capsules.

Preparation Process:

1. Granulation

The salvianolic acid T, (S)-salvianolic acid T, (R)-salvianolic acid T and other adjuvants listed in the formulation were sieved through a 100-mesh sieve, respectively. According to the formulation dosage, the salvianolic acid T, starch and sodium carboxymethyl starch were well blended according to equivalent progressively increasing method, a proper amount of 5% (w/v) PVP anhydrous ethanol was used to produce the soft materials, granulated with a 14-mesh sieve and dried at 50-60□ for 1 h. The magnesium stearate according to the formulation dosage was added to sieve the granule with 14-mesh sieve.

2. Encapsulation

The resulting granule was loaded into capsules.

Formulation Example 3 Preparation Injections of Salvianolic Acid T, (S)-Salvianolic Acid T, (R)-Salvianolic Acid T Formulation:

| Salvianolic acid T, (S)-salvianolic acid T, (R)-salvianolic acid T | 100 g |
| --- | --- |
| Mannitol | 100 g |
| Water for injection | up to 2500 mL |

The above formulation was prepared into 1000 units.

Preparation Process:

The salvianolic acid T, (S)-salvianolic acid T, (R)-salvianolic acid T were taken according to the formulation dosage, dissolved with 1000 ml of water for injection and stirred uniformly; the mannitol was taken according to the formulation dosage, dissolved with 500 ml of water for injection and added into the aforesaid solution, stirred uniformly, into which 0.5 g of activated carbon was added to stir at an invariant temperature for 30 min and filtered, the pH of the filtrate was adjusted to 4.5-5.0, diluted with water for injection to 2500 ml, filtered aseptically, loaded separately to obtain the product.

Formulation Example 4 Preparation Lyophilized Powder of the Salvianolic Acid T, (S)-Salvianolic Acid T, (R)-Salvianolic Acid T Formulation:

| Salvianolic acid T, (S)-salvianolic acid T, (R)-salvianolic acid T | 100 g |
| --- | --- |
| Mannitol | 100 g |
| Water for injection | 2000 mL |

The above formulation was prepared into 1000 unit;

Preparation Process:

The salvianolic acid T, (S)-salvianolic acid T, (R)-salvianolic acid T and mannitol were weighed according to the formulation dosage, and dissolved with 1500 ml of water for injection by stirring, into which 0.5 g of activated carbon was added for decolorization by stirring for 20 min, the solution was filtered through microvoid filter film (0.45 μm) to remove the carbon and diluted with water for injection up to 2000 ml. The resulting solution was filtered aseptically, packed separately and freeze dried to obtain the product.

Pharmacodynamic Example 1 The Effect of (S)-Salvianolic Acid T on Preventing Ligating Coronary Artery Acute Myocardial Infarction Materials 1. Subject Materials and Reagents (S)-salvianolic acid T, batch No: 120301, provided by Tasly Holding Group Academy, Aspirin enteric coated tablets: Spec: 100 mg/piece, Bayer healthcare Co., Ltd., batch No: BJ07160.

Sodium chloride injection of 0.9% (w/v), Nanjing Xiaoying Pharmaceutical Group Co. Ltd., batch No: 2012051205.

Chloral hydrate: AR, Sinopharm Chemical Reagent Co., Ltd., batch No: 20100111.

Red tetrazoline (TTC), Sinopharm Chemical Reagent Co., Ltd., batch No:F20040308.

Creatine kinase (CK) Assay kit, batch No: 20120917; lactic acid (LD) Assay kit, batch No: 20120919; malondialdehyde (MDA) Assay kit, batch No: 20120919; superoxide dismutase (SOD) Assay kit, batch No: 20120918; creatine kinase isoenzyme (CK-MB) Assay kit, batch No: 20120922; ATP enzyme Assay kit, batch No: 20120921. All provided by Nanjing Jiancheng Bioengineering Institute.

2. Main Apparatus:

HX-300 ventilator: Chengdu Taimeng Science and Technology Co., Ltd.

ECG-6511 electrocardiograph: Shanghai Photoelectric Medical Electronic Instrument Co., Ltd.

HH-2 Digital display thermostatic water bath: Guohua Electric Appliance Co., Ltd.

BS 224s type Electronic balance: Beijing Sartorius Instrument System Engineering Co., Ltd.

BS 110s type Electronic balance: Beijing Sartorius Instrument System Engineering Co., Ltd.

3. Experimental Animals:

SD rats, body-weight of 210-230 g, male, provided by Beijing Vital River Laboratory Animal Technology Co., Ltd., with the certificate No. of SCXK (Su) 2009-0001.

Experimental Methods and Results

1. Design of Administration Dose

Dose of the (S)-salvianolic acid T lyophilized powder was 20 mg/kg body-weight, 10 mg/kg body-weight. Aspirin: 30 mg/kg body-weight.

2. Experimental Methods

Clean male SD rats were taken and placed in groups randomly according to the body-weight, including pseudo operation group (distilled water), model group (distilled water), aspirin group, (S)-salvianolic acid T low-dose group, (S)-salvianolic acid T high-dose group, and there were 10 rats in each group. Each group of rats were administrated by gastric administration once a day, continuously for 10 days. Administration volume was 1 mL/100 g body-weight. 1 h after the end time of the administration, 300 mg/kg body-weight of chloral hydrate was injected by intraperitoneal injection, anaesthetized, fixed on back, sterilized on the surgical sites with iodine and alcohol successively, then opened chest at the third and forth ribs, and gave artificial respiration, exposed heart, ligated left anterior descending branch of coronary artery with medical atraumatic suture needle 5/0, closed the thoracic cavity rapidly and sterilized conventionally, the time of the operation procedure was less than 30 s, artificial respiration was continued for 1~2 min after the operation, 200 thousand units of penicillin was given by intramuscular injection (i. m.) to prevent influence. Recording standard II lead ECG at 5 minutes before surgery, 0 s, 1 min, 5 min, 15 min, 1 h, 4 h after the ligation, to investigate the changes of J point of ECG.

Taking out the heart immediately after the end of the experiment, washing away the blood with normal saline, cutting off the atrium and the bottom of the blood vessels, weighing the mass of the ventricle, cutting the ventricle into 5 pieces on average along the atrioventricular groove and putting them into 1% (w/v) TTC solution, dyeing in the water bath at a constant temperature of 37□ for 5 min, taking digital photos firstly after taking them out, then separating the unstained parts (that is, the infarct parts) and weighing to calculate the percentage of them in the mass of total ventricular (myocardial infarction percentage), and performing t test with ischemia model group. The formula for calculating the infarct percentage is as follows:

Infarct percentage (%)=(the mass of pale areas/the mass of the ventricle)×100%

After the blood was centrifuged at 2000 rpm for 25 minutes, separating the serum out, determining the content or activity of serum creatine kinase (CK), lactate dehydrogenase (LD), creatine kinase isoenzyme (CK-MB), malon-aldehyde (MDA), superoxide dismutase (SOD), ATPase. The results were showed in table 5, 6, 7 and FIG. 11.

As showed in table 5, the J points of ECG of each group of rats after coronary artery ligation operation were obviously higher than the ones before the operation (P<0.01), which illustrated the success of molding. Compared with the model group, 5 minutes after the operation, (S)-salvianolic acid T high-dose group could significantly inhibit the raise of J points (P<0.05); 15 minutes after the operation, (S)-salvianolic acid T high-dose group could significantly inhibit the raise of J points (P<0.05); 1 h and 4 h after the operation, aspirin group, (S)-salvianolic acid T high-dose group both could inhibit the raise of J points (P<0.05).

As showed in table 6, the myocardial infarction rates of the model group and each medication administration group were all obviously higher than pseudo operation group (P<0.01), which illustrated the success of molding. Compared with the model group, aspirin group, (S)-salvianolic acid T high-dose group both could significantly reduce the myocardial infarction rate (P<0.05).

TABLE 5

The effect of (S)-salvianolic acid T on the changes of J point (mv) of rats with myocardial infarction induced by coronary artery ligation ($\bar{x} \pm s$, n = 10)

| Group | dosage (mg/kg) | Before operation | After operation | | | | |
|---|---|---|---|---|---|---|---|
| | | | 1 min | 5 min | 15 min | 1 h | 4 h |
| Model group | | −0.010 ± 0.003 | 0.179 ± 0.042## | 0.205 ± 0.014## | 0.207 ± 0.045## | 0.205 ± 0.033## | 0.198 ± 0.009## |
| Aspirin group | 30 | −0.012 ± 0.005 | 0.172 ± 0.057## | 0.184 ± 0.024## | 0.166 ± 0.025## | 0.169 ± 0.036##▲ | 0.172 ± 0.021##▲ |
| (S)-salvianolic acid T low-dose group | 5 | −0.011 ± 0.003 | 0.176 ± 0.050## | 0.204 ± 0.010## | 0.185 ± 0.096## | 0.206 ± 0.036## | 0.194 ± 0.042## |
| (S)-salvianolic acid T high-dose group | 10 | −0.014 ± 0.005 | 0.169 ± 0.033## | 0.146 ± 0.031##▲ | 0.160 ± 0.027##▲ | 0.170 ± 0.014##▲ | 0.153 ± 0.028##▲ |

P < 0.05,

P < 0.01, conducting before-after self control at each time point before and after molding;

▲P < 0.05,

▲▲P < 0.01, compared with model group.

TABLE 7

The effect of (S)-salvianolic acid T on blood biochemical index of rats with myocardial infarction induced by coronary artery ligation

| Group | dosage (mg/kg) | MDA (nmol/ml) | LD (mmol/L) | SOD (U/ml) | CK (U/ml) | CK-MB (U/L) | Na$^+$—K$^+$-ATPase (μmolPi/10$^7$ RBC/h) |
|---|---|---|---|---|---|---|---|
| Pseudo operation group | | 4.85 ± 1.14 | 1.6 ± 0.19 | 239.4 ± 20.7 | 0.82 ± 0.19 | 745.2 ± 121.4 | 0.006 ± 0.001 |
| Model group | | 9.71 ± 2.39## | 2.07 ± 0.31## | 188.3 ± 28.5## | 1.74 ± 0.44## | 1176.4 ± 197.8## | 0.003 ± 0.001## |
| Aspirin group | 30 | 6.84 ± 0.97▲ | 1.75 ± 0.17▲ | 221.1 ± 24.7▲ | 1.01 ± 0.16▲▲ | 841.9 ± 20.3▲▲ | 0.005 ± 0.001▲ |
| (S)-salvianolic acid T low-dose group | 5 | 7.46 ± 1.07▲ | 1.67 ± 0.23▲ | 220.3 ± 32.6 | 1.18 ± 0.29▲ | 970.9 ± 225.1 | 0.004 ± 0.001▲ |

TABLE 7-continued

The effect of (S)-salvianolic acid T on blood biochemical index of rats with myocardial infarction induced by coronary artery ligation

| Group | dosage (mg/kg) | MDA (nmol/ml) | LD (mmol/L) | SOD (U/ml) | CK (U/ml) | CK-MB (U/L) | Na$^+$—K$^+$-ATPase ($\mu$molPi/10$^7$ RBC/h) |
|---|---|---|---|---|---|---|---|
| (S)-salvianolic acid T high-dose group | 10 | 6.72 ± 1.54▲ | 1.65 ± 0.24▲ | 241.7 ± 19.8▲▲ | 0.88 ± 0.22▲▲ | 846.7 ± 144.2▲▲ | 0.005 ± 0.006▲ |

P < 0.05,
P < 0.01, compared with pseudo operation group;
▲P < 0.05,
▲▲P < 0.01, compared with model group.

As showed in table 7, the MDA, LD, CK, CK-MB level of serum in model group were obviously higher than the pseudo operation group (P<0.01), while the SOD, Na$^+$-K$^+$-ATPase were obviously lower than the pseudo operation group (P<0.01), which indicated the success of molding. Compared with the model group, aspirin group, (S)-salvianolic acid T low-dose group, (S)-salvianolic acid T high-dose group could obviously reduce the content of MDA and LD in the serum of myocardial ischemia rats (P<0.05); aspirin group, (S)-salvianolic acid T high-dose group could obviously increase the serum SOD activity of myocardial ischemia rats (respectively was P<0.05, P<0.01); aspirin group, (S)-salvianolic acid T low-dose group, (S)-salvianolic acid T high-dose group could obviously the vitality of CK in the serum of myocardial ischemia rats (P<0.05, P<0.01); aspirin group, (S)-salvianolic acid T high-dose group could obviously reduce the vitality of CK-MB (P<0.01); aspirin group, (S)-salvianolic acid T low-dose group, (S)-salvianolic acid T high-dose group could obviously increase the the vitality of Na$^+$-K$^+$-ATPase.

Figure 11:
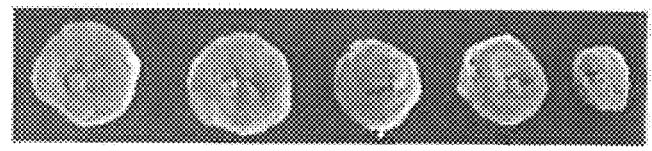
FIG. 11 illustrates heart biopsy diagrams of each group in the research on the effect of (S)-salvianolic acid T on acute myocardial infarction.
Figure 11:
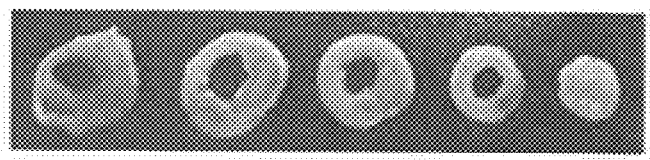
Figure 11:
Figure 11:
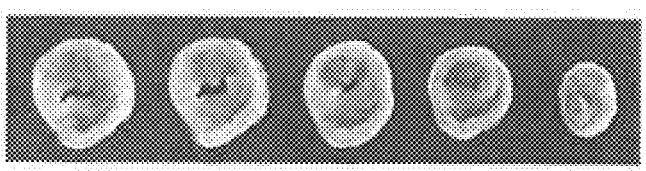
Figure 11:
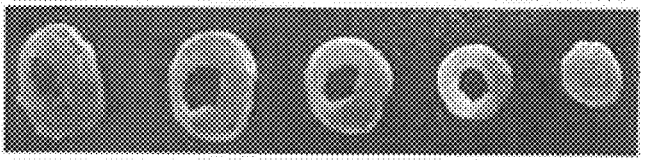

As showed in FIG. 11, (S)-salvianolic acid T high-dose group and aspirin group had the equal effect on preventing acute myocardial infarction induced by coronary artery ligation. A further test showed that, similar to (S)-salvianolic acid T, the (R)-salvianolic acid T high-dose group and aspirin group also had the equal effect on preventing acute myocardial infarction induced by coronary artery ligation.

Pharmacodynamic Example 2 Protective Effect of the (R)-Salvianolic Acid T on Experimental Acute Myocardial Ischemia in Rats Experimental Materials 1. Subject materials and reagents: pituitrin (Pit) injection was produced by Nanjing Xinbai Pharmaceutical Co., Ltd., with the batch No. of 070302. Normal saline was produced by Tianjin Tian'an Pharmaceutical Co., Ltd., with the batch No. of 201009231, specification: 500 ml/bottle. (R)-salvianolic acid T with a purity of more than 95% was provided by Institute of TASLY HOLDING GROUP.CO.LTD.

2. Main apparatus: MedLab 8-channel biophysiological recorder was produced by Nanjing Medease Science and Technology Co., Ltd.

3. Animals: SD rats, half male and half female in body-weight of 220-250 g, were provided by Beijing Vital River Laboratory Animal Technology Co., Ltd., with the certificate No. of SCXK (Jing) 2007-0001. All rats were fed with rat special diet (produced by Beijing Keaoxieli Diet Co., Ltd.) and tap water in animal feeding room at room temperature of 20-25□, illuminated for 12 h.

Experimental Methods

1. Design of Administration Dose

Administration dose of the (R)-salvianolic acid T lyophilized powder was 10 mg/kg body-weight in high-dose group; 5.0 mg/kg body-weight in low-dose group.

2. Grouping:

2.1 Screening of Animals: Before formal experiment, rats were injected via vena caudalis with pituitrin (Pit) (1 U/kg). Normal ECG and the ECG of 5 min after injection were recorded to observe J point elevation and T wave abnormality. Animals who had abnormal ECG before injection or who were insensitive to Pit were rejected.

2.2 Grouping of Animals: The desirable rats were divided into 3 groups randomly, respectively named □Model control group, □(R)-salvianolic acid T lyophilized powder low-dose group; □(R)-salvianolic acid T lyophilized powder high-dose group.

3. Experimental Methods: SD rats, in body-weight of 220-250 g, half male and half female, were randomly divided into groups, 10 animals in each group. The rats in the treatment groups were drenched with aqueous suspensions of different samples each day, while the rats in the model control group were drenched with equal volume of normal saline. All animals were consecutively administered for 7 days. 40 min after final administration, the rats were anesthetized and connected with devices to record lead II normal ECG. The pituitrin (Pit) was injected at a constant speed in the dosage of 1 U/kg body-weight via vena caudalis within about 10 s. ECG changes were recorded at 0 s, 5 s, 10 s, 15 s, 30 s, 45 s, 1 min, 2 min, 3 min, 4 min, 5 min, 10 min and 15 min after administration. Differences between pre injection and post injection of Pit of each group as well as between the treatment group and the model control group were compared to analyze changes of J point and T wave, and the data were analyzed by t-test.

Experimental Results

1. Effect on J Point

As shown in the results of table 8, compared with the model control group, the elevation extent of J point of ECG in (R)-salvianolic acid T high-dose group is less at 15 s, 30 s and 45 s in pituitrin-caused acute myocardial ischemia and the difference had statistical significance under the present experimental condition (P<0.05).

TABLE 8

The changes of J point in acute myocardial ischemia ($\bar{x} \pm s$, n = 10)

| Group | Time points | | | |
|---|---|---|---|---|
| | normal | 0 s | 15 s | 30 s |
| Model group | −0.060 ± 0.033 | −0.039 ± 0.037 | 0.021 ± 0.039 | −0.022 ± 0.028 |
| (R)-salvianolic acid T low-dose group | −0.054 ± 0.046 | −0.040 ± 0.027 | 0.023 ± 0.039 | −0.052 ± 0.022 |
| (R)-salvianolic acid T high-dose group | −0.049 ± 0.037 | −0.040 ± 0.039 | −0.069 ± 0.035* | −0.058 ± 0.035* |

| Group | Time points | | | |
|---|---|---|---|---|
| | 45 s | 1 min | 5 min | 10 min |
| Model group | −0.032 ± 0.042 | −0.006 ± 0.042 | −0.059 ± 0.041 | −0.035 ± 0.043 |
| (R)-salvianolic acid T low-dose group | −0.030 ± 0.041 | −0.016 ± 0.032 | −0.034 ± 0.052 | −0.025 ± 0.051 |
| (R)-salvianolic acid T high-dose group | −0.052 ± 0.031* | −0.016 ± 0.037 | −0.058 ± 0.049 | -0.061 ± 0.049 |

*$P < 0.05$, compared with model group.

As shown in the results of table 9, compared with the model control group, the elevation extent of T wave of ECG of (R)-salvianolic acid T high-dose group at 15 s and 30 s is less, and the difference had statistical significance under the present experimental condition ($P<0.05$).

TABLE 9

The changes of T wave in acute myocardial ischemia ($\bar{x} \pm s$, n = 10)

| Group | Time points | | | |
|---|---|---|---|---|
| | normal | 0 s | 15 s | 30 s |
| Model group | 0.098 ± 0.039 | 0.161 ± 0.097 | 0.271 ± 0.079 | 0.131 ± 0.089 |
| (R)-salvianolic acid T low-dose group | 0.101 ± 0.069 | 0.134 ± 0.104 | 0.211 ± 0.109 | 0.189 ± 0.120 |
| (R)-salvianolic acid T high-dose group | 0.099 ± 0.073 | 0.128 ± 0.106 | 0.150 ± 0.101* | 0.100 ± 0.095* |

| Group | Time points | | | |
|---|---|---|---|---|
| | 45 s | 1 min | 5 min | 10 min |
| Model group | 0.091 ± 0.087 | 0.160 ± 0.091 | 0.135 ± 0.097 | 0.110 ± 0.086 |
| (R)-salvianolic acid T low-dose group | 0.176 ± 0.137 | 0.151 ± 0.097 | 0.121 ± 0.101 | 0.142 ± 0.099 |
| (R)-salvianolic acid T high-dose group | 0.134 ± 0.105 | 0.145 ± 0.099 | 0.127 ± 0.104 | 0.150 ± 0.102 |

*$P < 0.05$, compared with the model group.

Conclusions

Compared with the model control group, the elevation extent of J point of ECG and T wave in (R)-salvianolic acid T high-dose group is less at 15 s and 30 s, and the difference had statistical significance ($P<0.05$). As shown in result, under this study, the (R)-salvianolic acid T (10.0 mg/kg) had effect of anti-acute myocardiac ischemia. A further experiment showed that, similar to (R)-salvianolic acid T, (S)-salvianolic acid had the similar effect of anti-acute myocardiac ischemia.

Pharmacodynamic Example 3
Free-Radicals-Trapping Reaction of the (S)/(R)-Salvianolic Acid T Due to their direct or indirect oxidation effect, the free radicals have been shown to take part in physiological and pathological process widely. In the presence of excess amount of free radicals, they always attack macromolecules in the body by oxidation. The salvianolic acid compounds are donors of phenolic hydroxyl group, having the structural basis for their antioxidant activity. In this study, 1,1-diphenyl-2-picryl-hydrazyl (DPPH) free-radical scavenging reaction model has been used to observe the free-radical scavenging activity of the (S)/(R)-salvianolic acid T.

1. Reagents and Apparatus

The (S)/(R)-salvianolic acid T with a purity of more than 95%, which was provided by Tasly Group Academy. Vitamin C and DPPH were purchased from SIGMA Inc. Ultraviolet spectrophotometer (UV-1800) was purchased from Beijing Rayleigh Analytical Instrument Co., Ltd.

2. Experimental Methods

The total reaction volume was 2 ml. 1 ml of the sample solutions at different concentrations in 80% methanol were added into 100 μM of DPPH methanol solution, mixed uniformly to allow the solution to react for 20 min at 25° C., in the dark. Absorbance of the reaction solution was measured at 517 nm. In this study, vitamin C was regarded as a positive control. Free-radical scavenging rate was calculated in accordance with the following equation:

Free-radical scavenging rate (%)=[1−$A_{sample}$/$A_{control}$]/$A_{control}$×100%

Wherein, the $A_{sample}$ means the absorbance of the tested samples, and $A_{control}$ means the absorbance of blank control.

3. Experimental Results

The (S)/(R)-salvianolic acid T had a much higher free-radical scavenging than that of the vitamin C, but there was no significant difference between the free-radical scavenging of the two isomers (P<0.05).

TABLE 10

The free-radical scavenging of (S)/(R)-salvianolic acid T

| | Sample (μg/ml) | | | | |
|---|---|---|---|---|---|
| | 0.625 | 1.25 | 2.5 | 5 | 10 |
| (S)-salvianolic acid T | 10.32 ± 0.81 | 28.77 ± 2.26 | 44.22 ± 1.95 | 86.01 ± 8.92 | 98.97 ± 5.41 |
| (R)-salvianolic acid T | 10.51 ± 0.73 | 28.15 ± 2.47 | 43.41 ± 1.85 | 85.59 ± 8.75 | 99.47 ± 5.14 |
| Vitamin C | 8.02 ± 0.47 | 15.56 ± 1.81 | 21.32 ± 1.89 | 56.29 ± 5.93 | 79.51 ± 7.26 |

Pharmacodynamic Example 4 Determination of Reducing Capacity of the (S)/(R)-Salvianolic Acid T To a certain extent, a potential for preventative antioxidation is represented by the reducing capacity of the drug. The study had been carried out on reducing capacity of the (S)/(R)-salvianolic acid T of the present invention.

1. Reagents and Apparatus

The (S)/(R)-salvianolic acid T with a purity of more than 95%, which was provided by Tasly group Academy. Analytically pure potassium ferricyanide was purchased from Tianjin No. 1 Chemical Reagent Factory. Analytically pure trichloroacetic acid was purchased from Sinopharm Chemical Reagent Co., Ltd. Analytically pure ferric chloride was purchased from Tianjin Fengchuan Chemical Reagent Science and Technology Co., Ltd. Vitamin C was purchased from SIGMA Inc. Ultraviolet spectrophotometer (UV-1800) was purchased from Beijing Rayleigh Analytical Instrument Co., Ltd. Refrigerated centrifuge (Z323K) was purchased from HEMMLE, German.

2. Experimental Methods 0.5 ml of 200 mM phosphate buffer (pH6.8) containing different concentrations of the (S)/(R)-salvianolic acid T and 0.5 ml of 1.0% (w/v) potassium ferricyanide solution were sucked respectively and cooled on an ice bath after being heated on a water bath (50□) for 20 min. 0.5 ml of 10% trichloroacetic acid solution was added and centrifuged at 1000 g/min for 10 min. 1.0 ml of the resulting supernatant was taken, into which 1.0 ml of distilled water and 0.2 ml of 0.1% (w/v) ferric chloride solution were added, stood still for 10 min and the absorbance was measured at 700 nm. Meanwhile, the blank experiment was carried out. Vitamin C is a strongly reducing substance, acting as positive control in this study. Reducing capacity of the sample is represented by subtracting the absorbance of the blank control from the absorbance of the tested sample. Thus, it means the higher absorbance, the stronger reducing capacity.

3. Experimental Results

Each reducing capacity of the (S)/(R)-salvianolic acid T was much stronger than that of vitamin C, there was no significant difference between the reducing capacity of the two (P<0.05).

TABLE 11

The reducing capacity of the (S)/(R)-salvianolic acid T

| | Sample (μg/ml) | | | | |
|---|---|---|---|---|---|
| | 3.125 | 6.25 | 12.5 | 25 | 50 |
| (S)-salvianolic acid T | 0.157 ± 0.027 | 0.215 ± 0.011 | 0.039 ± 0.012 | 0.771 ± 0.023 | 1.573 ± 0.036 |
| (R)-salvianolic acid T | 0.152 ± 0.034 | 0.212 ± 0.009 | 0.042 ± 0.011 | 0.761 ± 0.018 | 1.561 ± 0.026 |

Pharmacodynamic Example 5 Anti-Pulmonary Fibrosis Experiment of (S)/(R)-Salvianolic Acid T in Mice Pulmonary fibrosis is a common reaction and complication after lung injury, the pathological changes of which are diffuse alveolar inflammation, formation of lung fibroblastic foci and repeated repair and excessive deposition of extracellular matrix. Pulmonary fibrosis usually ends with permanent loss of respiratory function, and lacks of effective means of prevention and treatment. The mice pulmonary fibrosis induced by bleomycin is a common model used for researching on human pulmonary fibrosis, oxygen free radical produced directly and indirectly by bleomycin in this model is one of the mechanisms that trigger the pulmonary fibrosis.

1. Reagents and Apparatus

The (S)/(R)-salvianolic acid T with a purity of more than 95%, which was provided by Tasly group Academy. Superoxide dismutase (SOD) kit, catalase (CAT) kit, peroxidase (POD) kit, malondialdehyde (MDA) kit were all purchased from Nanjing Jiangcheng Bioengineering Institute. The bleomycin was purchased from SIGMA.

2. Animals

Kunming mice, all female, with body weight of 22-25 g, were provided by Beijing Vital River Laboratory Animal Technology Co., Ltd., and fed in a condition of a temperature of 23±2° C., a relative humidity of 65%-75%, and a light period of 12 h:12 h.

3. Experimental Methods

Dividing the 40 mice into 4 groups: □ normal control group, given nasal dripping of normal saline, drenched with normal saline; □ model control group:given nasal dripping of bleomycin, drenched with normal saline; □(S)-salvianolic acid T group (16 mg/kg): given nasal dripping of bleomycin, drenched with (S)-salvianolic acid T solution; □(R)-salvianolic acid T group (16 mg/kg): given nasal dripping of bleomycin, drenched with (R)-salvianolic acid T solution; 10 mice in each group.

On the first day of the experiment, the mice were anesthetized with chloral hydrate, each mouse was given disposable nasal dripping of 50 μg bleomycin to establish the pulmonary fibrosis model. On the second day of the experiment, two treatment groups were drenched with (S)/(R)-salvianolic acid T, the model group and the normal group were drenched with equal volume of normal saline, once each day, 3 consecutive weeks. On the 21th day of the experiment, serum was separated from the blood collected from the orbital vein to detect TGF-β1, the mice were killed to take lungs, ground with double distilled water (the ratio of lungs and double distilled water was 1:5 (w/v)) into tissue homogenate, centrifuged to detect the MDA, superoxide dismutase (SOD), catalase (CAT), peroxidase (POD) in the tissues.

Statistical method: The results were all showed by x±s, analyse by One-factor Analysis of Variance between groups using statistical software, pairwise comparison was done with two groups of Independent-Samples t test.

4. Experimental Results

The effect on the pulmonary fibrosis in mice induced by bleomycin: compared with the normal mice, the TGF-β1 in the lungs of mice with pulmonary fibrosis induced by bleomycin increased by 9.96 times, the MDA increased by 1.83 times, antioxidase SOD, POD, CAT reduced by 1.5 times, and serum TGF-β1 also increased by 4.44 times, and the model was made successfully. (S)/(R)-salvianolic acid T both could inhibit the increase of TGF-β1 in serum of the mice induced by bleomycin (table 12), preventing the reduce of SOD, POD. CAT in lungs of the mice induced by bleomycin (table 13).

TABLE 12

The effect of (S)/(R)-salvianolic acid T on the factor levels in tissues and serum of the mice induced by bleomycin (x ± s, n = 10)

| Group | Serum TGF-β1 (ng/L) | Tissue TGF-β1 (pg/g) | MDA (μg/g) |
|---|---|---|---|
| Normal group | 145 ± 19 | 129 ± 17 | 241 ± 24 |
| Model group | 651 ± 124 | 1350 ± 264 | 472 ± 54 |
| (S)-salvianolic acid T group | 263 ± 35** | 541 ± 51** | 324 ± 33** |
| (R)-salvianolic acid T group | 254 ± 29** | 562 ± 69** | 311 ± 29** |

*: $P < 0.05$; **$P < 0.01$, compared with the model group.

TABLE 13

The effect of (S)/(R)-salvianolic acid T on the oxidase level in tissues of the mice induced by bleomycin (x ± s, n = 10)

| Group | SOD (U/g) | POD (U/g) | CAT (U/g) |
|---|---|---|---|
| Normal group | 61.2 ± 6.7 | 21.3 ± 2.0 | 27.4 ± 2.4 |
| Model group | 33.6 ± 5.2 | 11.5 ± 1.6 | 14.9 ± 1.4 |
| (S)-salvianolic acid T group | 57.3 ± 4.9* | 15.3 ± 2.1** | 24.9 ± 2.3** |
| (R)-salvianolic acid T group | 52.2 ± 5.1** | 16.4 ± 1.9* | 23.1 ± 2.9** |

*$P < 0.05$; **$P < 0.01$, compared with the model group.

Pharmacodynamic Example 5 Inhibition Effect of (S)/(R)-Salvianolic Acid T on Fibroblasts Induced by TGF-β

The excessive proliferation of fibroblasts induced by TGF-β and the differentiation of fibroblasts activated to myofibroblasts play an important role in the formation of pulmonary fibrosis, inhibiting the signal transduction of TGF-β could prevent the proliferation and activation of lung fibroblasts, is one of the Important means for preventing and treating pulmonary fibrosis effectively.

1. Reagents and Apparatus

The (S)/(R)-salvianolic acid T with a purity of more than 95%, which was provided by Tasly group Academy. DMEM culture medium, MTT, recombination TGF-β1 were purchased from Sigma company. Penicillin and streptomycin, produced by CSPC Pharmaceutical Group Limited. Fetal bovine serum, produced by Hangzhou Sijiqing Biological Engineering Materials institute. Collagen assay kit, produced by Biocolor company. Laminin (LN) RIA Kit was purchased from Beijing Beifang Biotechnology Institute.

EL-800X type Microplate Reader, purchased from BIO-TEK company; $CO_2$ incubator purchased from Thermo company; flow cytometry purchased from FACS company.

2. Cell Strain

L929 cell, purchased from Cell Institute of Academy of Military Medical Sciences 3. Experimental Methods L929 cells with a cell population of $5 \times 10^7$/L adjusted by DMEM culture solution containing 10% fetal bovine serum were seeded into 96 well plate, cultured for 24 h. Supplementing the same culture medium containing 2 μg/L TGF-β1 and (S)/(R)-salvianolic acid T of different concentrations. There were 6 multiple pores in each group, final concentration of (S)/(R)-salvianolic acid T was set as 0, 1, 3, 10, 20, 40, 80, 150 μmol/L. Removing medium after being cultured for 72 h, assaying the cell activity by MTT method.

Figure 12:
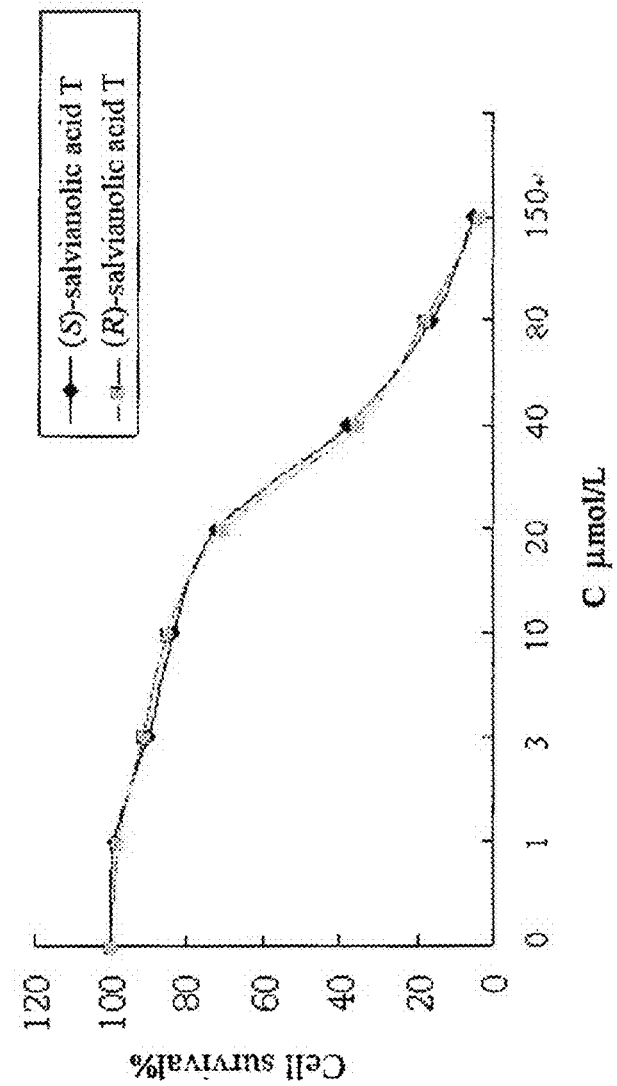
FIG. 12 illustrates the inhibitory effect of (R)-salvianolic acid T and (S)-salvianolic acid T on L929 cell proliferation induced by TGF-β1.

4. Experimental Results (S)-salvianolic acid T and (R)-salvianolic acid T had inhibition effect on proliferation of L929 cells induced by TGF-β1 (FIG. 12), the $IC_{50}$ of the (S)-salvianolic acid T was 26.1 μmol/L, the the $IC_{50}$ of the (R)-salvianolic acid T was 26.9 μmol/L, there was no significant difference between the two.

The results of the pharmacodynamic test in the present invention shows that, the salvianolic acid T of the present invention has the activity of preventing acute myocardial infarction and acute myocardial ischemia, excellent free radical scavenging and reducing capacity, as well as the activity of treating pulmonary fibrosis.

What is claimed is:

1. A pharmaceutically acceptable oral preparation in the form of a tablet or a capsule consisting of 30 to 95 weight percent of salvianolic acid T represented by the structural formula (I), its pharmaceutically acceptable salts, chiral isomers, solvates of salvianolic acid T represented by the structural formula (I):

Structural formula (I)

and pharmaceutical carrier, wherein the oral preparation is effective to treat pulmonary fibrosis.

2. A method of making the oral preparation of claim 1 consisting of:
   (A) making the salvianolic acid T by the steps of (1a)-(1b):
      (1a) extracting Radix Salviae Miltiorrhizae crude drug with water, concentrating the filtrate to obtain a water extract, then adding alcohol to precipitate and obtain a supernatant, concentrating the supernatant to obtain an alcohol extract; and,
      (1b) diluting the alcohol extract of the step (1a) in water, applying the diluted alcohol extract on a macroporous absorbent resin, washing the resin with an acidic aqueous solution to remove impurities, and then eluting the resin with ethanol to obtain an ethanol eluent, concentrating the ethanol eluent to obtain an extract; and,
   (B) pressing or molding the preparation into a tablet or capsule.

3. The method according to claim 2, wherein, in the step (1a), the said Radix Salviae Miltiorrhizae crude drug or the mixture of Radix Salviae Miltiorrhizae and other crude drugs are decoction pieces, crushed particles or powders, the said other crude drugs are Radix *Notoginseng* or Radix Astragali or the combination of the two that which are compatible with the Radix Salviae Miltiorrhizae.

4. The method according to claim 2, wherein, in the step (1a), the said water-extraction is as follows: decocting the crude drug with water of 4-8 times the volume of the crude drug for 1.5-4 h; filtrating; concentrating the filtrate to obtain a water extract with a relative density of 1.10-1.30 (80° C.).

5. The method according to claim 2, wherein, in the step (1b), the weight ratio of the crude drug used in the step (1a) to the macroporous absorbent resin is 5:1-1:1.

6. The method according to claim 2, wherein, in the step (1b), 4-10 times of 50%-95% (v/v) ethanol is used to wash the column, then the eluent is concentrated to obtain an extract without alcoholic smell.

7. A method of making the oral preparation of claim 1 consisting of:
   (A) making the salvianolic acid T by the steps of (1)-(4):
      (1) dissolving salvianolic acid B in water, and heating;
      (2) adjusting the pH of the reaction liquid obtained in the step (1) to be acidic,
      (3) purifying an extract obtained in the step (2) by employing a preparative high pressure liquid chromatograph, with C18 reversed phase silica gel column as the chromatographic packing, acetonitrile-water-formic acid as the eluent, and carrying out isocratic elution or gradient elution, with a detection wavelength of 280 nm and monitoring the elution process by high performance liquid chromatography,
      (4) collecting eluent containing salvianolic acid T from step (3) and, concentrating the eluent to obtain the salvianolic acid T; and
   (B) pressing or molding the preparation into a tablet or capsule.

8. The method according to claim 2, wherein, in the step (2), the said high pressure liquid chromatograph is dynamic axial high pressure liquid chromatograph, the chromatographic packing is C18 reversed phase silica gel column, dissolving the reaction liquid the pH of which is adjusted in the step (1) or the extract obtained in the said step (1b) with mobile phase, the said mobile phase is acetonitrile:water:formic acid (volume ratio)(10:90:1)–(90:10:1); the eluent uses the above ratio of the mobile phase, the elution is isocratic elution or gradient elution; the flow rate is 300 mL/min; the detection wavelength is 280 nm; high performance liquid chromatography is used to monitor the elution process, collecting the components the retention time of which is 21.2-24.0 min, concentrating to dry, obtaining salvianolic acid T sample.

9. A method of treating at least one of acute myocardial infarction, acute myocardial ischemia, and pulmonary fibrosis disease, wherein said method comprises administering the oral preparation of claim 1 to a patient.

10. The oral preparation of claim 1 wherein the tablets are selected from sugar-coated tablets, film-coated tablets, enteric-coated tablets, and buccal tablets.

11. The method of claim 2 wherein the tablet is selected from a sugar-coated tablet, a film-coated tablet, an enteric-coated tablet, and a buccal tablet.

12. The method according to claim 7, wherein, in the step (1), the mass ratio of the said salvianolic acid B to the said aqueous solution is 1:0.1-1:100000, the reaction temperature is 10-150° C., the reaction time is 10 min to 24 h.

13. A pharmaceutically acceptable oral preparation in the form of a tablet or a capsule consisting of:
   30 to 95 weight percent of salvianolic acid T represented by the structural formula (I), its pharmaceutically acceptable salts, chiral isomers, solvates of salvianolic acid T represented by the structural formula (I):

Structural formula (I)

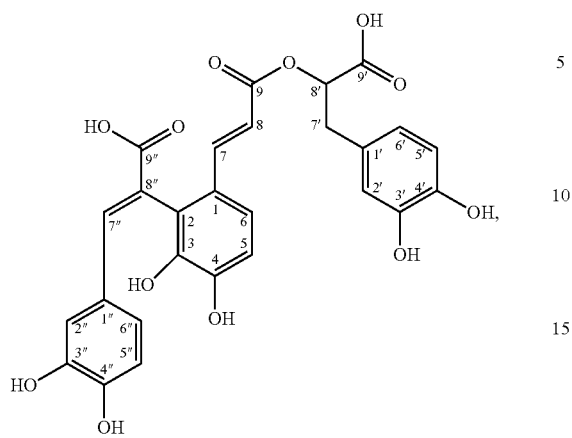

and a pharmaceutically acceptable carrier selected from the group consisting of sugar-alcohol; amino acid; vitamin C; disodium EDTA; EDTA calcium sodiumsodium pyrosulfite; inorganic salts; stearate; inorganic acid; organic acid salts; oligosaccharide; polysaccharide; maltose; glucose; fructose; sucrose; lactose; gelatin; polyvinylpyrrolidone; glycerol; agar; polyethylene glycol; phospholipids; kaolin; talc powder; and combinations thereof, and wherein the oral preparation is effective to treat pulmonary fibrosis.

* * * * *